US009415031B2

(12) United States Patent
Viswanath et al.

(10) Patent No.: US 9,415,031 B2
(45) Date of Patent: Aug. 16, 2016

(54) D-SERINE TRANSPORTER INHIBITORS AS PHARMACEUTICAL COMPOSITIONS FOR THE TREATMENT OF VISUAL SYSTEM DISORDERS

(71) Applicant: Allergan, Inc., Irvine, CA (US)

(72) Inventors: Veena Viswanath, Irvine, CA (US); Alan C. Foster, San Diego, CA (US); Yong-Xin Li, Mission Viejo, CA (US); Ursula V. Staubli, Laguna Beach, CA (US); Lauren M. Luhrs, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 46 days.

(21) Appl. No.: 14/248,228

(22) Filed: Apr. 8, 2014

(65) Prior Publication Data

US 2014/0221453 A1 Aug. 7, 2014

Related U.S. Application Data

(62) Division of application No. 13/479,803, filed on May 24, 2012, now Pat. No. 8,735,451.

(60) Provisional application No. 61/490,652, filed on May 27, 2011.

(51) Int. Cl.
| | |
|---|---|
| *A61K 31/195* | (2006.01) |
| *A01N 37/44* | (2006.01) |
| *A61K 31/216* | (2006.01) |
| *A61K 31/196* | (2006.01) |
| *A61K 31/198* | (2006.01) |
| *A61K 31/401* | (2006.01) |
| *A61K 45/06* | (2006.01) |
| *A61K 31/405* | (2006.01) |
| *A61K 31/197* | (2006.01) |

(52) U.S. Cl.
CPC .............. *A61K 31/216* (2013.01); *A61K 31/196* (2013.01); *A61K 31/197* (2013.01); *A61K 31/198* (2013.01); *A61K 31/401* (2013.01); *A61K 31/405* (2013.01); *A61K 45/06* (2013.01)

(58) Field of Classification Search
CPC ............ A61K 2300/00; A61K 31/196; A61K 31/198; A61K 31/401; A61K 31/197; A61K 31/216; A61K 31/405; A61K 45/06
USPC .................. 514/423, 548, 561, 562, 563, 567
See application file for complete search history.

(56) References Cited

U.S. PATENT DOCUMENTS

| | | | |
|---|---|---|---|
| 3,644,643 A | 2/1972 | Krantz | |
| 4,166,452 A | 9/1979 | Generales | |
| 4,256,108 A | 3/1981 | Theeuwes | |
| 4,265,874 A | 5/1981 | Bonsen et al. | |
| 8,735,451 B2 * | 5/2014 | Foster | A61K 31/196 514/561 |
| 8,741,955 B2 * | 6/2014 | Foster | A61K 31/196 514/563 |
| 2002/0010212 A1 | 1/2002 | Javitt | |
| 2005/0159488 A1 | 7/2005 | Javitt | |
| 2014/0200254 A1 * | 7/2014 | Foster | A61K 31/196 514/423 |
| 2015/0174095 A1 * | 6/2015 | Foster | A61K 9/0048 514/423 |

FOREIGN PATENT DOCUMENTS

| | | |
|---|---|---|
| EP | 1612206 | 1/2006 |
| EP | 2077110 | 7/2009 |
| WO | WO03-077998 | 9/2003 |

OTHER PUBLICATIONS

Cooke, Sam et al, Visual Experience Induces Long-Term Potentiation in the Primary Visual Cortex, Journal of Neuroscience, Dec. 2010, 16304-16313, 30(48).

Dun, Y. et al, Functional and Molecular Analysis of D-Serine Transport in Retinal Muller Cells, Experimental Eye Research, 2007, 191-199, 84.

Lynch, James et al, (L)-Phenylglycine, But Not Necessarily Other alpha2delta Subunit Voltage-Gated Calcium Channel Ligands, Attenuates Neuropathic Pain in Rats, Pain, 2006, 136-142, 125.

Matsuo, H et al, Cloning, Functional Characterization and Localization of ASC-1; A High Affinity Amino Acid Transporter for D-Serine, Annual Meeting of the Society for Neuroscience, 2001, 917.2, 27.

O'Brien, Kylie et al, D-Serine Uptake by Isolated Retinas is Consistent with ASCT-Mediated Transport, Neuroscience Letters, 2005, 58-63, 385.

Ribeiro, Catia et al, Glial Transport of the Neuromodulator D-Serine, Brain Research, 2002, 202-209, 929.

Scharfman, H.E. et al, N-Methyl-D-Aspartate Receptors Contribute to Excitatory Postsynaptic Potentials of Cat Lateral Geniculate Neurons Recorded in Thalamic Slices, Proc Natl Acad Sci, Jun. 1990, 4548-4552, 87.

Shao, Zongjun et al, Functional and Immunocytochemical Characterization of D-Serine Transporters in Cortical Neuron and Astrocyte Cultures, Journal of Neuroscience Research, 2009, 2520-2530, 87.

Stevens, Eric et al, D-Serine and Serine Racemase are Present in the Vertebrate Retina and Contribute to the Physiological Activation of NMDA Receptors, Proceedings of the National Academy of Sciences of the United States of America, May 27, 2003, 6789-6794, 100 (11).

Thomas E. Krahe and Alexandre E. Medina, Activation of NMDA Receptors Is Necessary for the Recovery of Cortical Binocularity, Mar. 16, 2010, Journal of Neurophysiology 103: 2700-2706,, 103.

(Continued)

*Primary Examiner* — My-Chau T Tran
(74) *Attorney, Agent, or Firm* — Jonathan Bass

(57) ABSTRACT

The present invention relates to pharmaceutical compositions comprising D-serine transporter inhibitors and therapeutic methods using such pharmaceutical compositions in methods for the treatment of visual system disorders and the enhancement of the visual function.

20 Claims, 18 Drawing Sheets

(56) References Cited

OTHER PUBLICATIONS

Thomsen, C. et al, Characterisation of D-Serine Transporter and Functional Modulation of NMDA Receptors, Abstract of the Annual Meeting of the Society for Neuroscience, 2001, 917.3, 27.
Wielgus, A.R. et al, Blue Light Induced A2E Oxidation in Rat Eyes—Experimental Animal Model of Dry AMD, Photochemical & Photobiological Sciences, 2010, 1505-1512, 9.
Broer et al., "The Astroglial ASCT2 Amino Acid Transporter as a Mediator of Glutamine Efflux"; J. Neurochem., vol. 73, No. 5, pp. 2184-2194, 1999.
Esslinger, "Nc-Aryl glutamine analogues as probes of the ASCT2 Neutral Amino Acid Transporter Binding Site", Bioorganic Med Chern 13:1111-1118, (2005).
Foster, et al. "Glutamate- and GABA-Based CNS Therapeutics", Curr Opin Pharmacol; 6 : 7-17, (2006).
Grewer C and Grabsch E "New Inhibitors for the Neutral Amino Acid Transporter ASCT2 Reveal its Na+ -Dependent Anion Leak", J Physiol 557.3:747-759, (2004).
Harveit et al., "Neurotransmitter Receptors Mediating Excitatory Input to Cells in the Cat Lateral Geniculate Nucleus. II Nonlagged Cells", Journal of Neurophysiology, vol. 63, No. 6, Jun. 1990.
Henneberger, et al. "Long Term Potentiation Depends on Release of D-Serine From Astrocytes", Nature. 463(7278): 232-236. doi:10.1038/nature08673, 2010.
Johnson, et al. "Glycine Potentiates the NMDA Response in Culture Mouse Brain Neurons", Nature vol. 325, pp. 529-531, 1987.
Labrie, et al.; "The involvement of the NMDA receptor D-serine/glycine site in the pathophysiology and treatment of schizophrenia"; Neuroscience and Biobehavioral Reviews 34, 351-372; (2010).
Mothet, et al. "D-Serine is an Endogenous Ligand for the Glycine Site of the N-methyl-D-Aspartate Receptor" Proc Natl Acad Sci 97:4926-4931, (2000).
Paoletti and Neyton, "NMDA Receptor Subunits: Function and Pharmacology", Current Opinion in Pharmacology, 7:39-47, 2007.
Pinilla-Tenas et al., "Transport of Proline and Hydroxyproline by the Neutral Amino-Acid Exchanger ASCT1", J. Membrane Biol. 195, 27-32 (2003).
Regan, "Rapid objective refraction using evoked brain potentials"; Investigative Ophthalmology; 12, 669-679, 1973.
Reminton's Pharmaceutical Sciences, Mack Publishing Company, Easton, Pa., 16th Edition, 1980.
Ribeiro et al., "Glial Transport of the neuromodulator D-Serine", Brain Research 929, 202-209, (2002).
Rosenberg, et al., "Neuronal release of D-serine: a physiological Pathway Controlling Extracellular D-Serine Concentration", FASEB Journal article fj.09-147967. Published online Apr. 6, 2010.
Rutter et al., "Evidence From Gene Knockout Studies Implicates Asc-1 as the Primary Transporter Mediating D-Serine Reuptake in The Mouse CNS", European Journal of Neuroscience, vol. 25, pp. 1757-1766, 2007.
Yang et al., "Contribution of Astrocytes to Hippocampal Long-Term Potentiation Through Release of D-Serine", PNAS, vol. 100, No. 25, pp. 15194-15199, 2003.
Shafqat et al., "Cloning and Expression of a Novel Na+-dependent Neutral Amino Acid Transporter Structurally Related to Mammalian Na+/Glutamate Cotransporters", Journal of Biological Chemestry, vol. 268, No. 21, pp. 15351-15355, 1993.
Stevens et al., "D-Serine and Serine Racemase Are Present in The Vertebrate Retina and Contribute to the Physiological Activation of NMDA receptors", PNAS, vol. 100, No. 11, pp. 6789-6794, 2003.
Torres-Zamorano et al., "Sodium-Dependent Homo- and Hetero-Exchange of Neutral Amino Acids Mediated by the Amino Acid Transporter ATB", Biochemical and Biophysical Research Communications 245, 824-829 (1998).
Utsunomiya-Tate et al., "Cloning and Functional Characterization of a System ASC-like Na1-dependent Neutral Amino Acid Transporter", The Journal of Biological Chemistry, vol. 271, No. 25, Issue of Jun. 21, pp. 14883-14890, 1996.
Xie et al., « Lack of the Alanine—Serine—Cysteine Transporter 1 Causes Tremors, Seizures, and Early Postnatal Death in Mice, Brain Research 1052, pp. 212-221, (2005).
Yamamoto et al., Functional Identification of ASCT1 Neutral Amino Acid Transporter As the Predominant System for the Uptake of L-Serine in Rat Neurons in Primary Culture, Neuroscience Research 49, pp. 101-111, (2004).
Tachikawa et al., "Inner Blood-Retinal Barrier Mediates L-Isomer-Predominant Transport of Serine", Sep. 2011,Journal of Pharmaceutical Sciences, Vol. 100, No. 9, pp. 3892-3903.
Patent Cooperation Treaty, Notification of Transmittal of the International Search Report and the Written Opinion of the International Searching Authority, or the Declaration, Form PCTIISN220, Int. App. No. PCT/US2012/09396, Aug. 1, 2012.

* cited by examiner

Figure 1: Inhibition of D-serine transport into rat brain synaptosomes and rat hippocampal astrocytes in culture by amino acid analogs.

| Compound | IC$_{50}$ in Astrocytes (µM) | IC$_{50}$ in Synaptosomes (µM) |
|---|---|---|
| L-serine | 57.9 | 9.6 |
| D-serine | 1581 | 9.4 |
| L-glutamine | 1641 | 943 |
| L-asparagine | 57.2 | 668 |
| L-GPNA | 3096 | 453 |
| L-glutamate-γ-benzyl ester | 3000 | 62 |
| L-4-fluorophenylglycine | 27.9 | 258 |
| L-4-hydroxyphenylglycine | 142.1 | 101 |
| DL-2-fluorophenylglycine | 1571 | 348 |
| L-phenylglycine | 89.4 | 217 |
| L-proline | 2271 | >10,000 |
| L-trans-4-hydroxyproline | 38.9 | >10,000 |
| S-benzyl-L-cysteine | 424 | 86 |
| S-phenyl-L-cysteine | 597 | 29.3 |

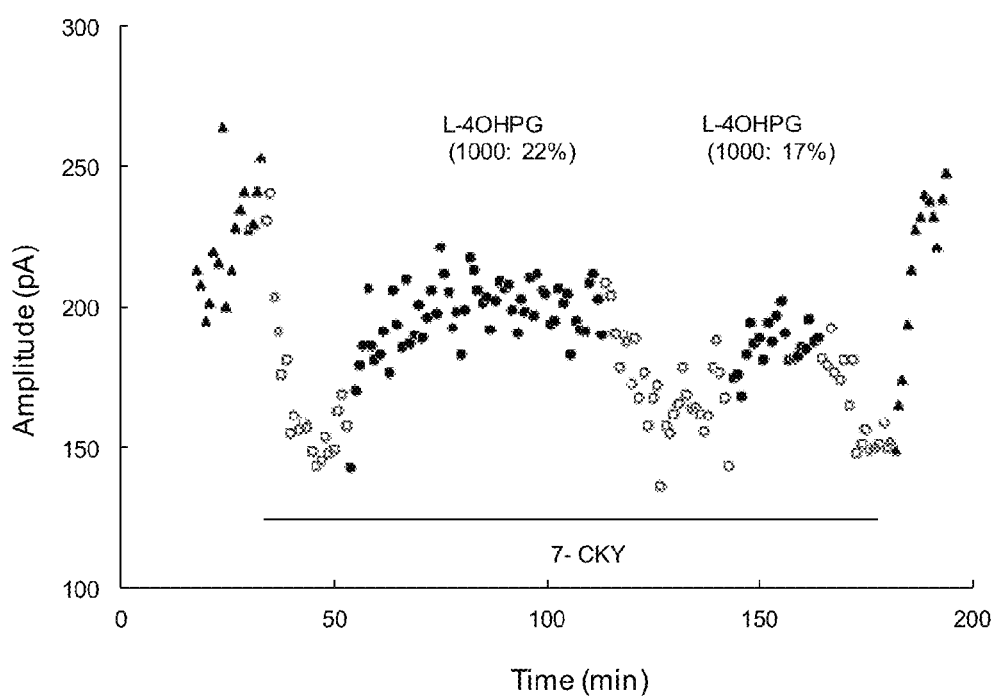
Figure 1A: Electrophysiological Recording from Rat Hippocampal Slices: L-4OHPG (L-4-hydroxyphenylglycine, 1000 μM) Potentiates NMDA Receptor-Mediated Excitatory Postsynaptic Currents (EPSC)

Figure 1B: Dose-response for L-4OHPG enhancement of NMDA Receptor-Mediated Excitatory Postsynaptic Currents (EPSC)
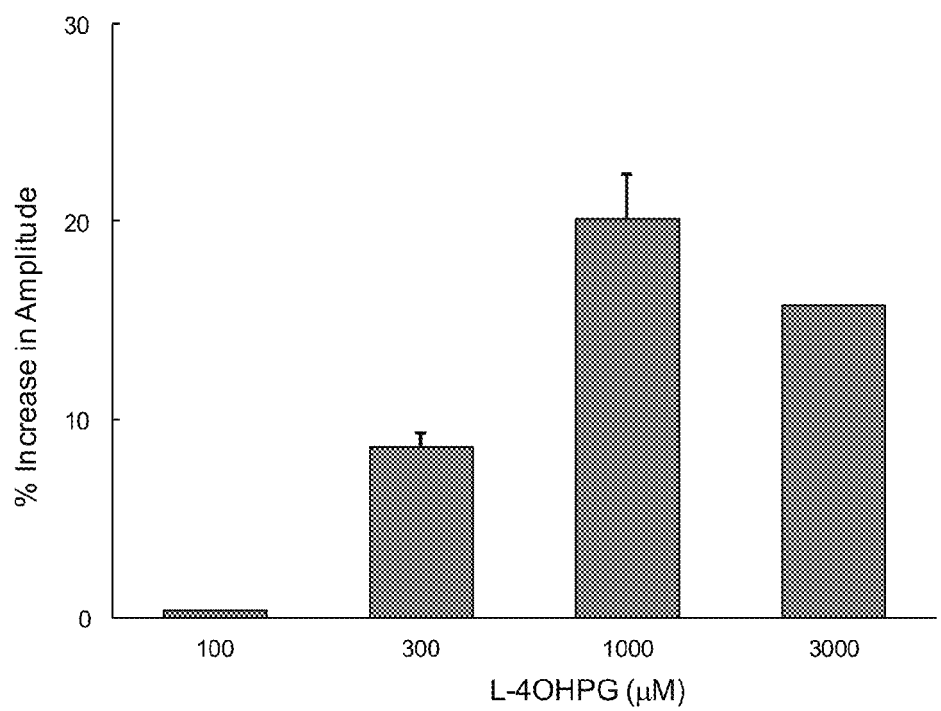

Figure 2: Comparison of $IC_{50}$ values for inhibition of transport in astrocytes and HEK cells expressing ASCT1 and ASCT2 in comparison with the threshold concentrations required to enhance LTP in the rat visual cortex slice. NA = not applicable.

| Compound | $IC_{50}$ Astrocytes (µM) | $IC_{50}$ ASCT1 (µM) | $IC_{50}$ ASCT2 (µM) | LTP Threshold (µM) |
|---|---|---|---|---|
| L-serine | 94 | 292 | 822 | NA |
| D-serine | 2592 | 3937 | 4913 | 3 |
| L-glutamine | 41*   4713* | 3373 | 541 | NA |
| L-asparagine | 108 | 656 | 674 | 3 |
| L-GPNA | 57*   4135* | >10,000 | 1133 | 100 |
| L-4-fluorophenylglycine | 83.3 | 377 | 437 | 0.3 |
| L-4-hydroxyphenylglycine | 283 | 1322 | 1728 | 10 |
| DL-2-fluorophenylglycine | 1572 | >3000 | >3000 | >300 |
| L-phenylglycine | 228 | 1217 | 945 | 10 |
| L-proline | 1780 | 2139 | >10,000 | NA |
| L-trans-4-hydroxyproline | 16*   3047* | 188 | 3475 | 3 |
| L-cyclopropylglycine | 180 | 948 | 428 | 1 |

\* values for high and low affinity components

NA = not applicable.

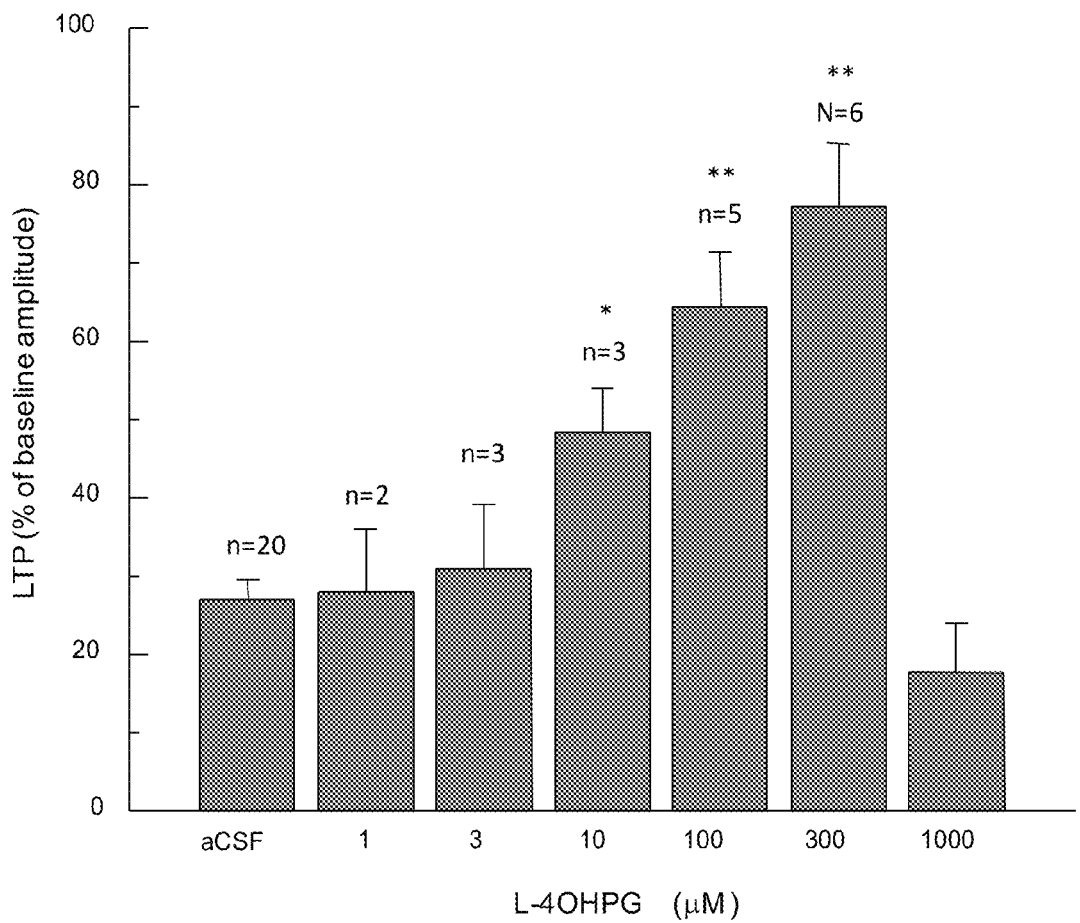
Figure 2A: L-4OHPG facilitates LTP in Primary Visual Cortex Layer III

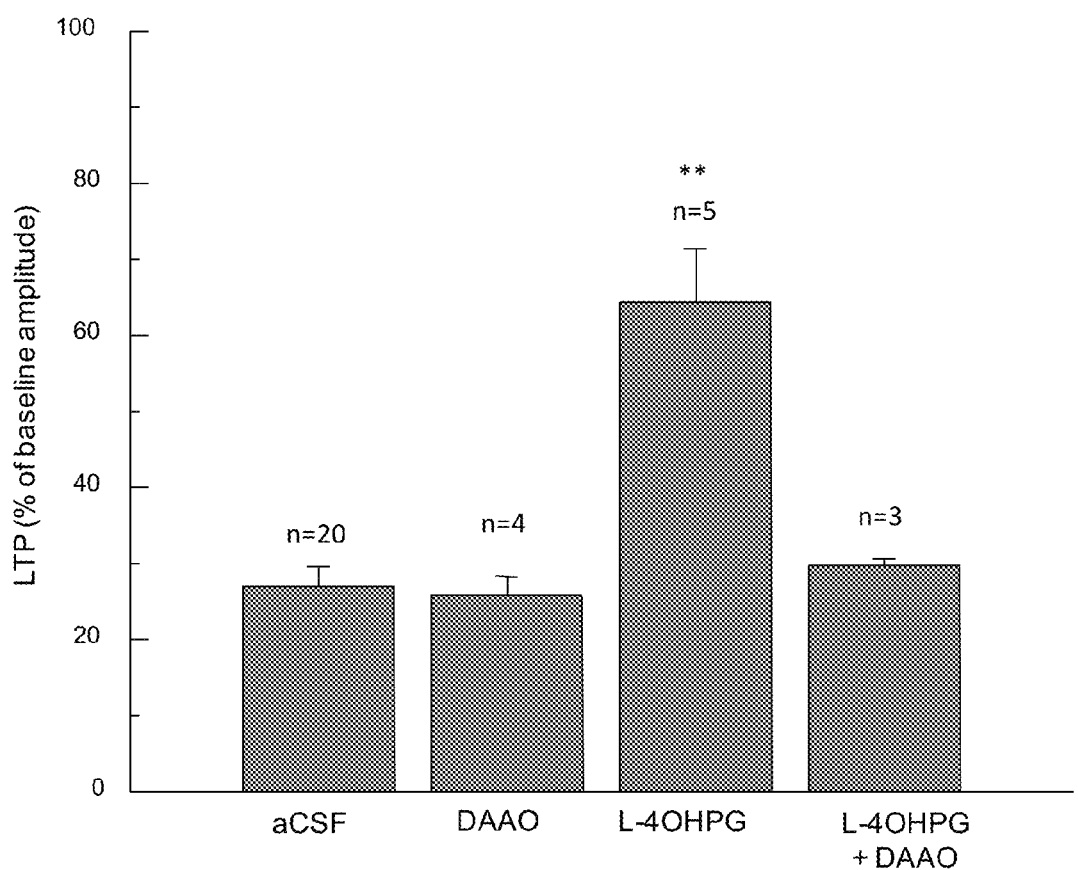
Figure 2B: 100 µM L-4OHPG LTP facilitation effect is blocked by D-amino acid oxidase (D-AAO)

Figure 3A: Correlation between inhibition of neuronal D-serine transport and enhancement of LTP in the rat visual cortex slice
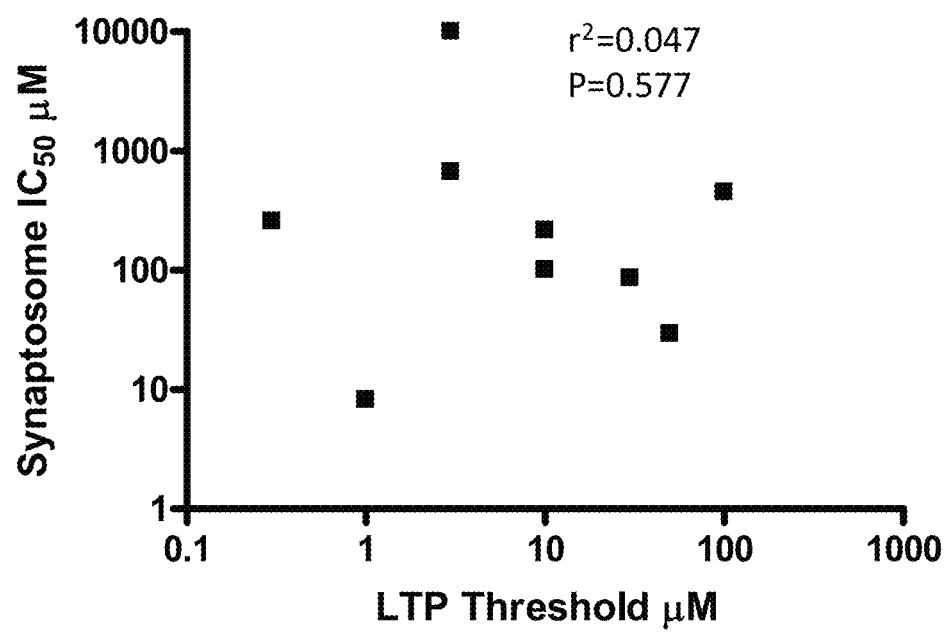

Figure 3B: Correlation between inhibition of astrocyte D-serine transport and enhancement of LTP in the rat visual cortex slice
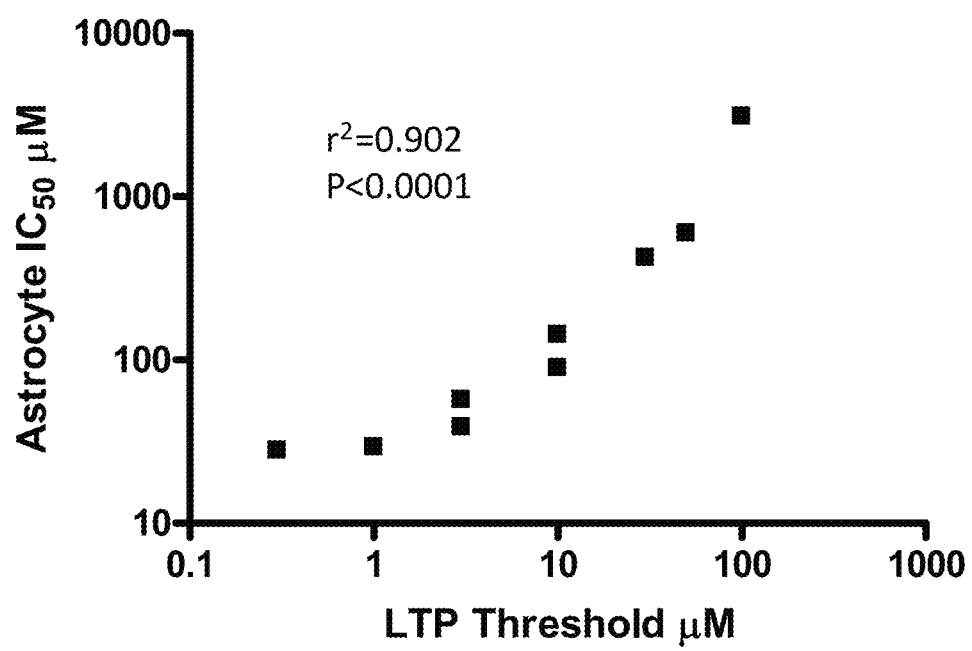

Figure 4: Two-component inhibition of [$^3$H]D-serine transport into astrocytes by L-glutamine and L-t-4OHPro and IC$_{50}$ values for the individual components
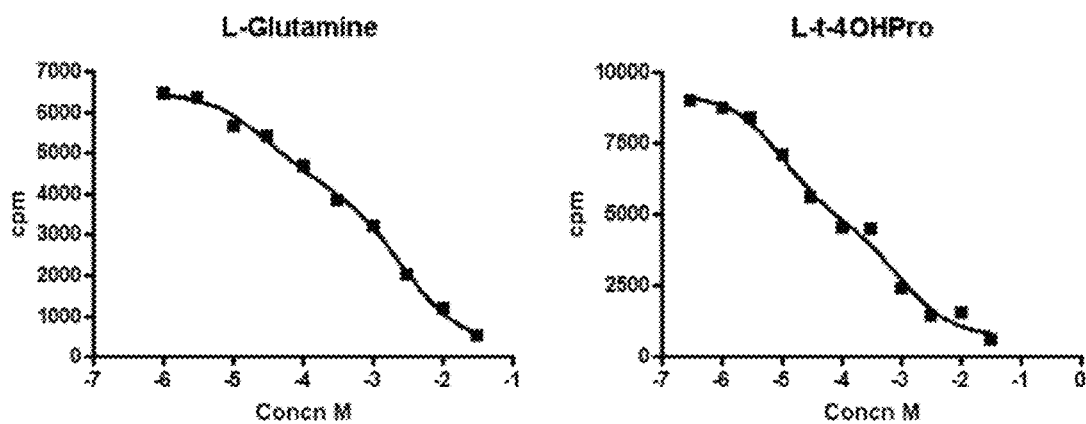
| Compound | Component 1 IC$_{50}$ μM | Component 2 IC$_{50}$ μM | Component 1 Fraction (%) |
|---|---|---|---|
| L-glutamine | 26.9 | 2737 | 36.7 |
| L-t-4OHPro | 17.2 | 2989 | 61.1 |

Figure 5: Inhibition of [³H]L-serine transport into parental HEK cells and HEK cells expressing ASCT1 and ASCT2 by L-glutamine and L-t-4OHPro. SLC1A4 is the gene name for ASCT1 and SLC1A5 is the gene name for ASCT2.
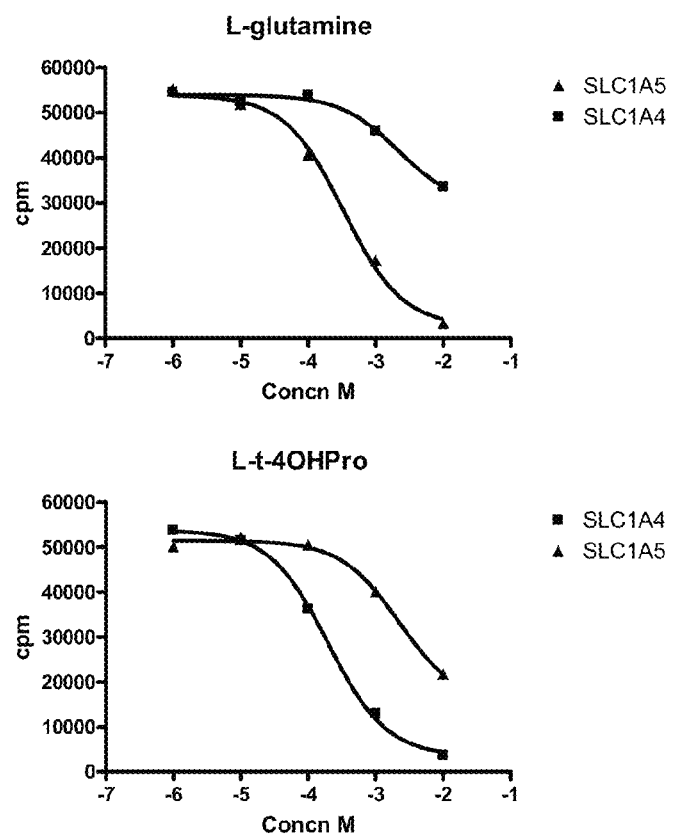
| IC$_{50}$ µM | ASCT1 (SLC1A4) | ASCT2 (SLC1A5) |
|---|---|---|
| L-glutamine | 3373 | 541 |
| L-t-4OHPro | 188 | 3475 |

Figure 6A: Transport of [$^3$H]D-serine by HEK cells expressing ASCT1 (SLC1A4) and ASCT2 (SLC1A5). The sodium-dependent transport of D-serine was similar in both cell lines.
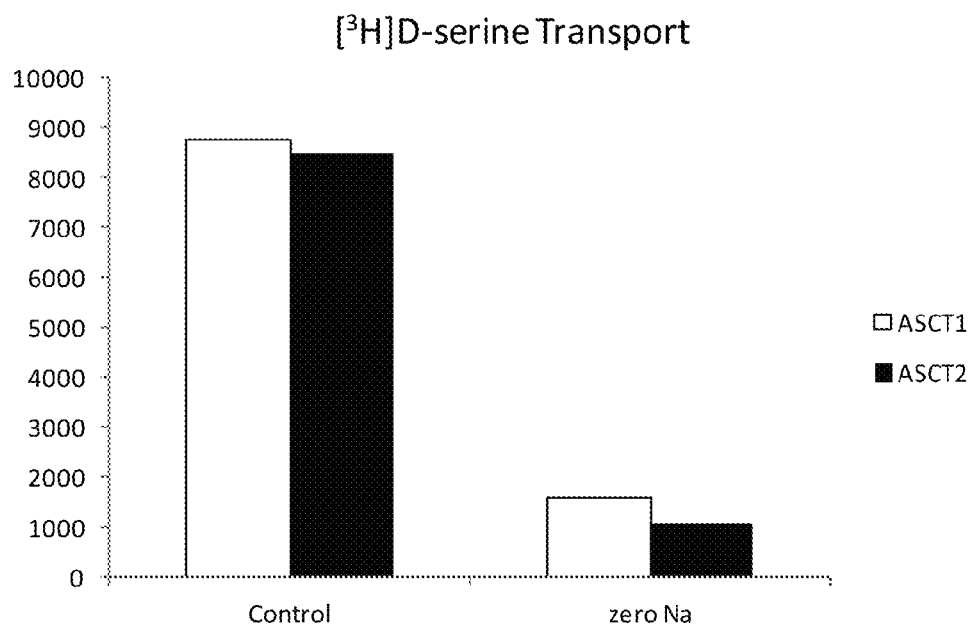

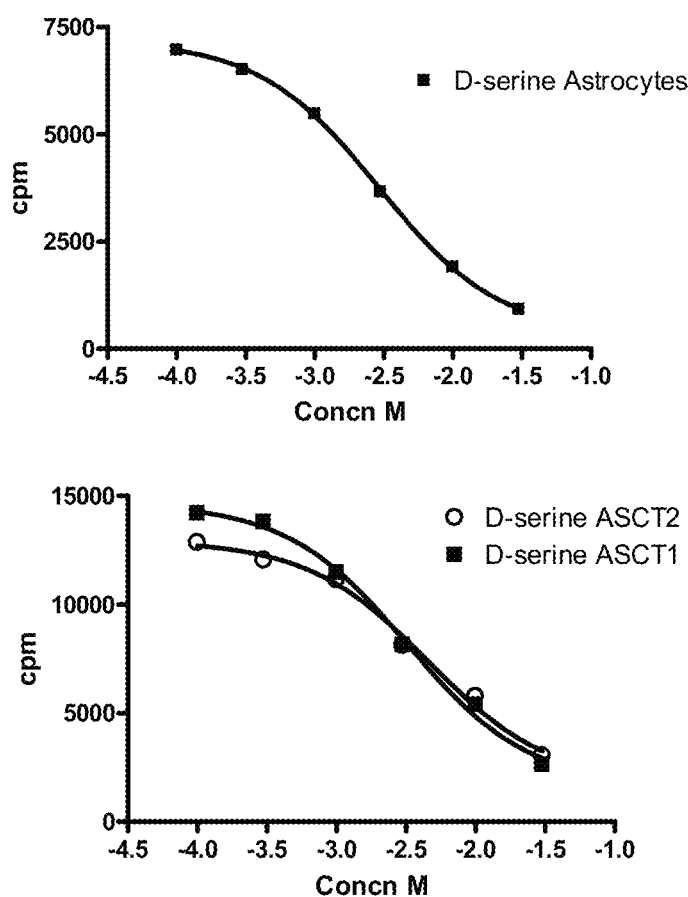
Figure 6B: Inhibition of transport into astrocytes and HEK cell lines by D-serine

Figure 7: Correlations between the ability of compounds to inhibit transport in HEK cells expressing ASCT1 and ASCT2 and the threshold concentration for LTP enhancement in the visual cortex
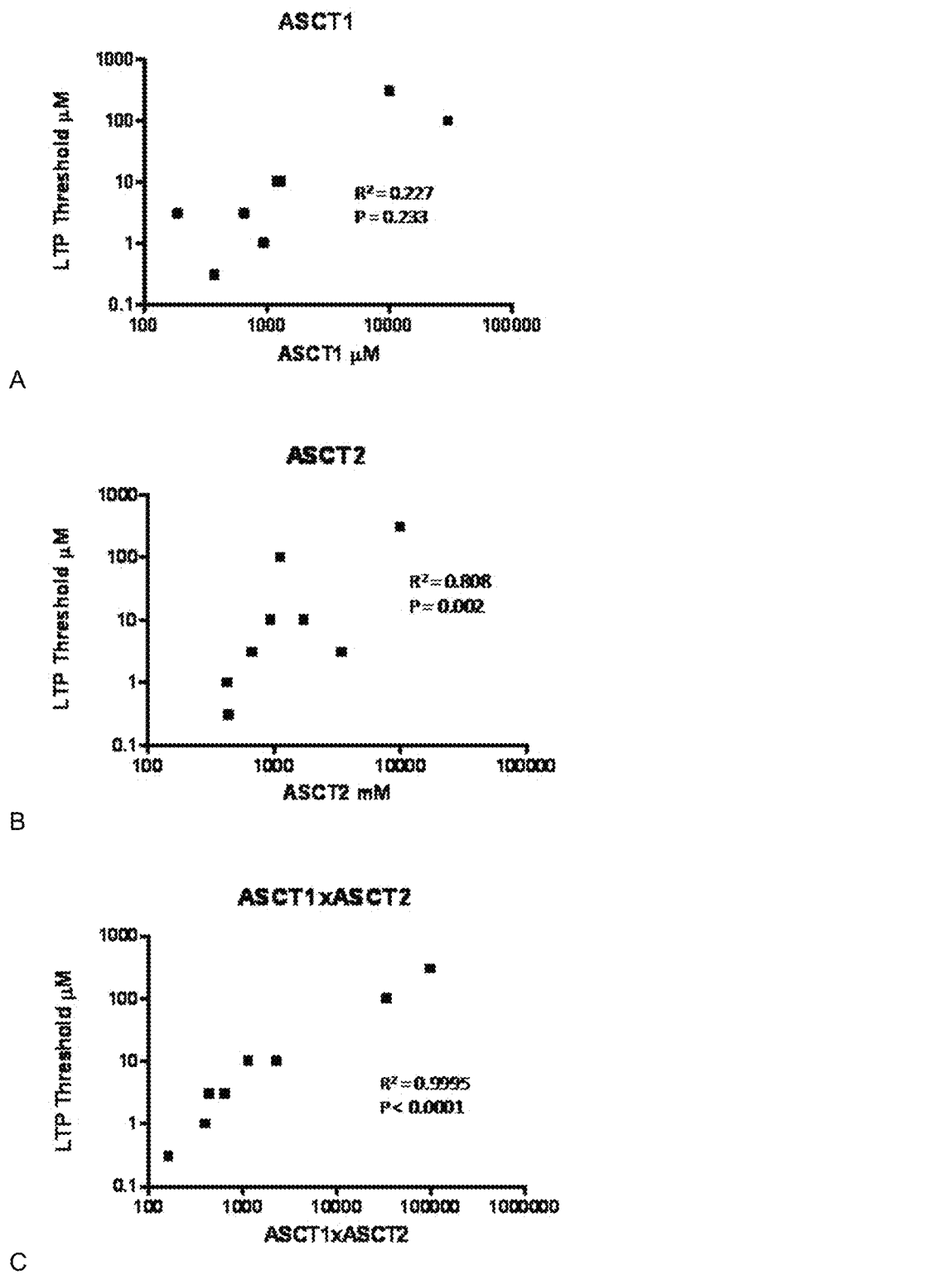

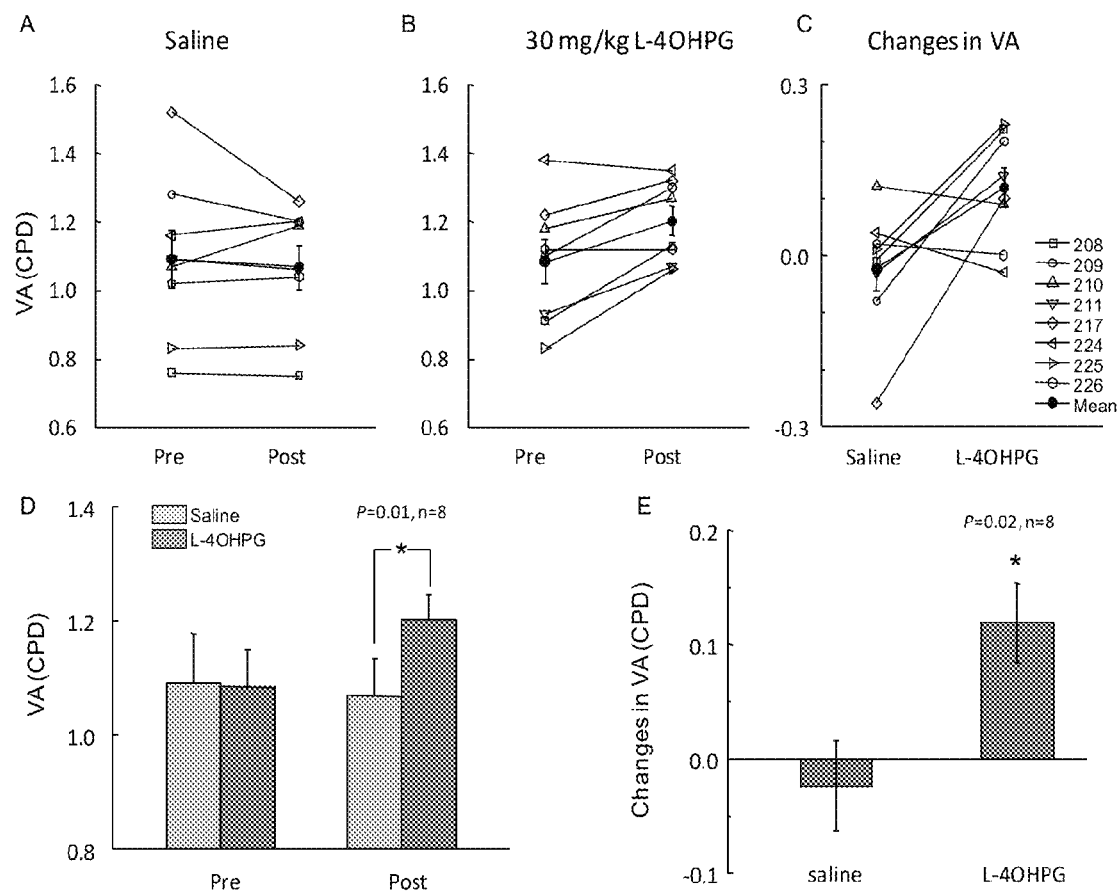
Figure 8: In Vivo Analysis of Acute Neuroenhancement Effect of LHPG on Visual Acuity of Rat: L-4OHPG enhance visual acuity in normal rats as assessed by sweep VEP

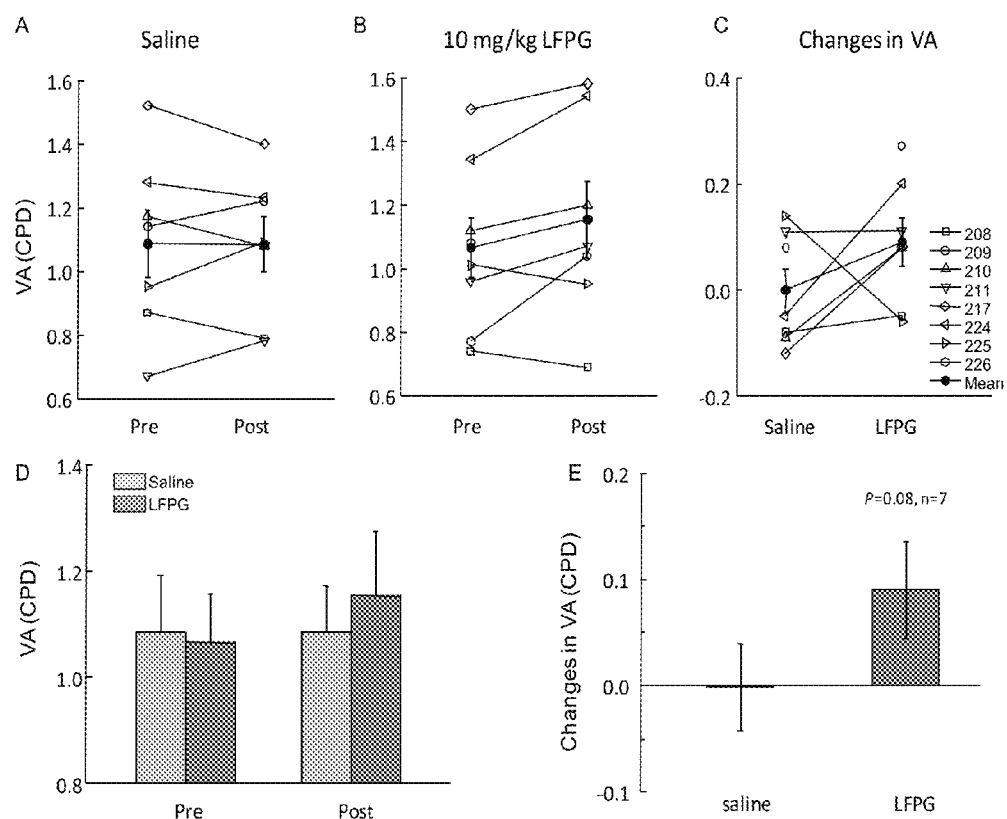
Figure 9: L-4FPG enhance visual acuity in normal rats as assessed by sweep VEP

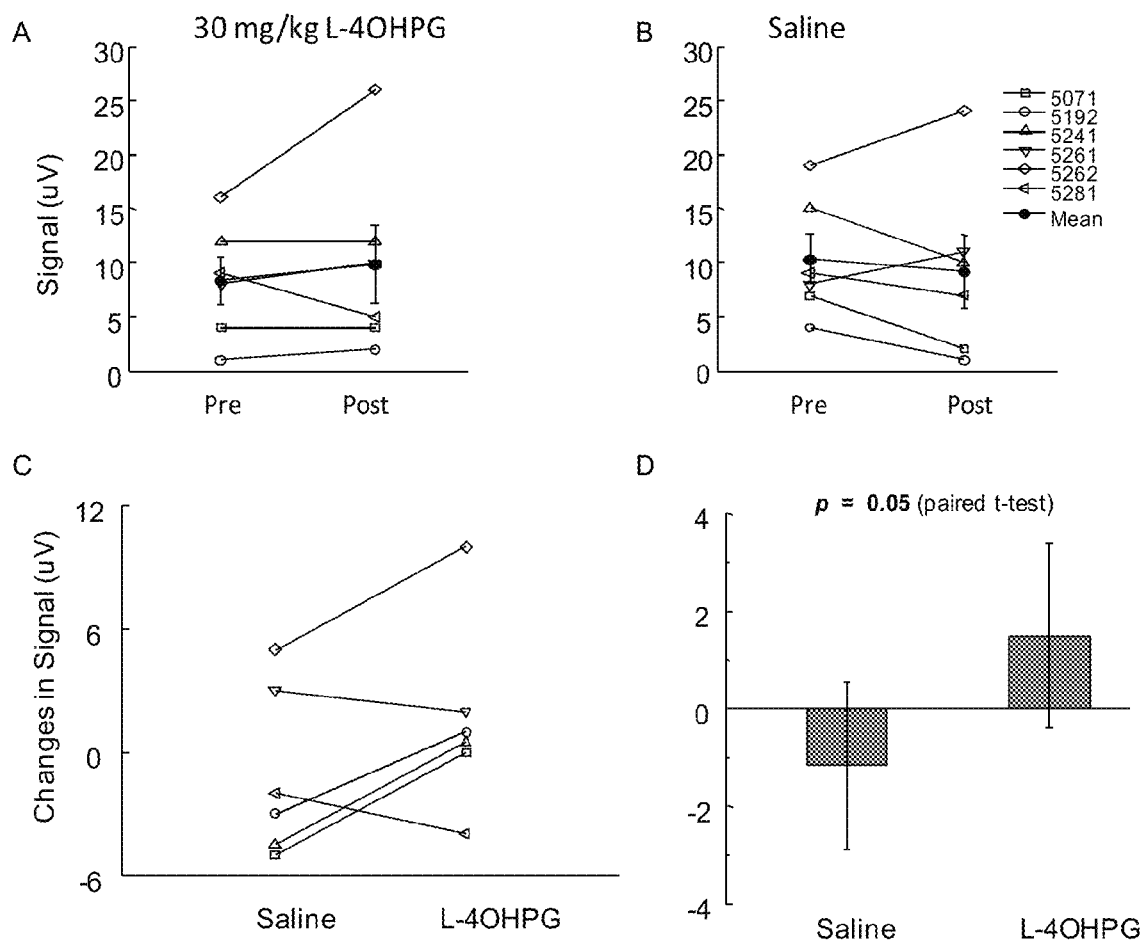
Figure 10: Effects of L-4OHPG on VEP of ONC rats (6 weeks after ONC (1s), 0.2 cpd)

Figure 11: Visual enhancement effect of 4-OHPG in Rabbits
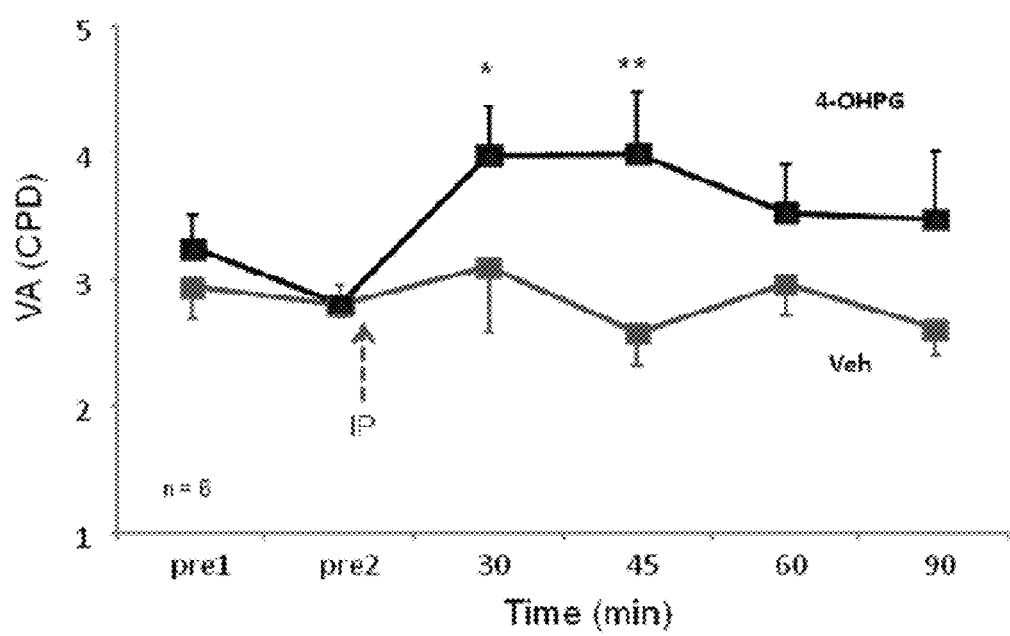

Figure 12: 4-FPG improved contrast sensitivity impaired by Blue-light treatment in LE rats
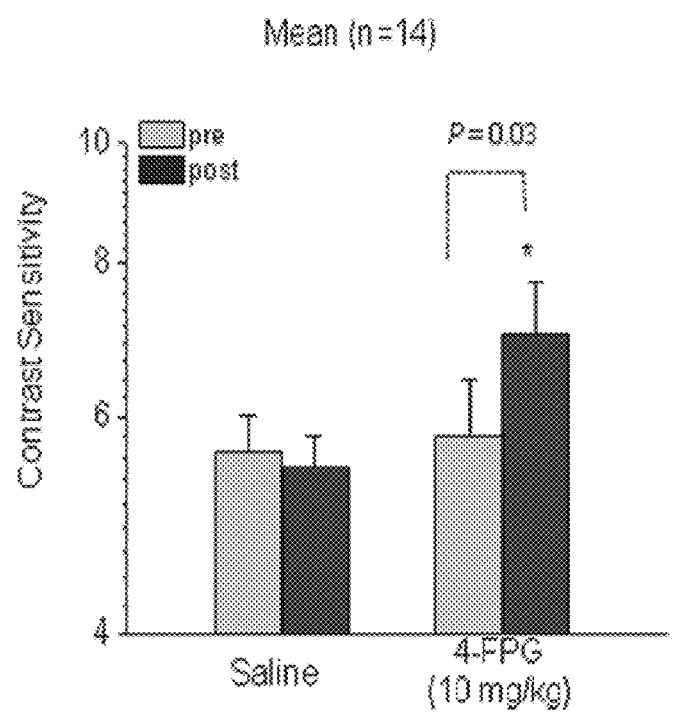

D-SERINE TRANSPORTER INHIBITORS AS PHARMACEUTICAL COMPOSITIONS FOR THE TREATMENT OF VISUAL SYSTEM DISORDERS

CROSS-REFERENCE TO RELATED APPLICATION

This application is a divisional patent application of U.S. Non-Provisional patent application Ser. No. 13/479,803 filed May 24, 2012, which claims the benefit of U.S. Provisional Patent Application No. 61/490,652 filed on May 27, 2011, which are incorporated here by reference in their entirety.

FIELD OF THE INVENTION

The present invention relates to pharmaceutical compositions comprising D-serine transporter inhibitors and therapeutic methods using such pharmaceutical compositions in methods for the treatment of visual system disorders and the enhancement of the visual function.

BACKGROUND

Neuronal circuits in the central nervous system rely on the release of chemical neurotransmitters from specialized connections called synapses for communication. The major excitatory neurotransmitter is the amino acid glutamate, and release of glutamate from a pre-synaptic terminal elicits a response through activation of several types of receptors. One of the sub-types of glutamate receptors, the N-methyl-D-aspartate (NMDA) receptor, plays a major role in neuronal communication and in the plasticity of synaptic responses that occurs under both physiological and pathophysiological conditions.

NMDA receptors are ligand-gated cation channels comprised of a tetrameric assembly of NR1, NR2 and NR3 subunits (Paoletti and Neyton, 2007). They are unique amongst neurotransmitter receptors in that they require occupation of two separate recognition sites for activation. An acidic amino acid site where glutamate binds, is located on the NR2 subunits, and a neutral amino acid (or co-agonist) site is located on the NR1 sub-unit. The endogenous co-agonist for this site was originally thought to be glycine, but more recent evidence indicated that D-serine is also an endogenous co-agonist. In fact, in higher brain regions D-serine may be the dominant co-agonist. Occupation of the co-agonist site is essential for glutamate (or a glutamate analog) to activate the NMDA receptor, and in native assays the removal of glycine or D-serine by exogenously-applied degradative enzymes can reduce or abolish NMDA receptor-mediated responses. For example, in the rat hippocampal slice, application of the D-serine metabolizing enzyme, D-amino acid oxidase (D-AAO), completely prevents the induction of long-term potentiation (LTP) a form of synaptic plasticity whose initiation is dependent on NMDA receptor activation (Yang et al., 2003). This suggests that the dominant co-agonist in this case is D-serine, since glycine is not a substrate for D-AAO.

The mechanisms that regulate extracellular D-serine, and therefore govern how NMDA receptors are activated, are not well understood. In keeping with other neurotransmitters and neuromodulators, it is likely that transporters on the cell surface are involved in regulating synaptic levels of D-serine. Amino acid transporters usually prefer L-amino acids, however D-serine has been shown to be a substrate for certain transporters. These include the heterodimeric transporter asc-1 (SLC3A2/SLC7A10) which has micromolar affinity for D-serine, ASCT2 (SLC1A5), ATB$^{0+}$ (SLC7A9) and PAT1-4 (SLC36A1-4). Based on the tissue and cellular localization, the primary candidates for transporters that regulate synaptic D-serine levels are asc-1 (neuronal) and ASCT2 (glial). The related transporter ASCT1 (SLC1A4) also has been localized to neurons and glia, however it has been reported that D-serine is not a substrate for ASCT1 (Shafqat et al., 1993). None of these transporters are selective for D-serine, and their substrates are typically small neutral amino acids such as serine, alanine, cysteine and threonine. They also are known to function as exchangers that can flux their substrates both into and out of cells. Consequently, it has been unclear if these transporters are responsible primarily for the net uptake or the net release of D-serine and other substrates. Considering that asc-1 has the highest known affinity for D-serine, it has been thought that this transporter is primarily responsible for removing D-serine from the extracellular space (Rutter et al., 2007). In support of this, the asc-1 knock-out mouse has a phenotype that includes increased excitability (Xie et al., 2005).

In the visual system, NMDA receptors are important mediators of glutamate-mediated neurotransmission and synaptic plasticity. This occurs at all levels of the visual axis, including neurons in the retina, in the central neurons that receive retinal ganglion cell input in the lateral geniculate nucleus and the superior colliculus, and in the visual cortex. Based on experiments using D-AAO, D-serine has been shown to be an endogenous co-agonist involved in NMDA-receptor-mediated synaptic responses in the retina (Stevens et al., 2003) NMDA receptors have also been shown to mediate synaptic responses in the lateral geniculate (Harveit & Heggelund, 1990; Scharfman et al., 1990) and the visual cortex (ie the primary pathways that transduce visual information). In the visual cortex, NMDA receptors mediate the phenomenon of long-term potentiation (LTP), an important form of synaptic plasticity. NMDA receptor-dependent LTP occurs in many brain regions and is viewed as a mechanism of synaptic strengthening that is fundamental to the establishment and maintenance of appropriate synaptic connections. In the hippocampus, for example, LTP has been studied as a synaptic surrogate of learning and memory. In visual cortex neurons, LTP mediates stimulus-specific response potentiation, a form of experience-dependent plasticity that contributes to visual function (Cooke and Bear, 2010).

In retinal diseases such as glaucoma and macular degeneration, loss of the vision arises from degeneration or malfunction of retinal cells. Consequently, the normal neuronal transmission along the visual pathway is disrupted in the affected parts of the visual field. One strategy to remedy this loss of function would be to enhance the visual neurotransmission that remains unaffected by disease to compensate for the region of impairment. In addition, enhancing the plasticity of neuronal connections that occurs in the adult visual system could lead to the establishment of new neuronal connections that replace the lost function and improve visual performance.

Enhancing NMDA receptor activity by increasing the extracellular levels of D-serine would boost visual performance and compensate for the loss of vision resulting from retinal disease. As a result, we have discovered compounds that inhibit the transport of D-serine and enhance NMDA receptor-mediated synaptic responses. We identified the D-serine transporters that are important for regulating NMDA receptor-mediated LTP in the visual cortex, and we demonstrated that D-serine transport inhibitors improve visual function in animal models of retinal disease.

SUMMARY OF THE INVENTION

The present invention relates to the use of pharmaceutical compositions comprising D-serine transporter inhibitor compound(s) in methods for the treatment of visual system disorders.

Visual system disorders which may be treated with the D-serine transport inhibitors include macular edema, dry and wet macular degeneration, choroidal neovascularization, diabetic retinopathy, acute macular neuroretinopathy, central serous chorioretinopathy, cystoid macular edema, and diabetic macular edema, uveitis, retinitis, choroiditis, acute multifocal placoid pigment epitheliopathy, Behcet's disease, birdshot retinochoroidopathy, syphilis, lyme, tuberculosis, toxoplasmosis, intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; retinal arterial occlusive disease, anterior uveitis, retinal vein occlusion, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy, angioid streaks, familial exudative vitreoretinopathy, and Eales disease; traumatic/surgical conditions such as sympathetic ophthalmia, uveitic retinal disease, retinal detachment, trauma, photocoagulation, hypoperfusion during surgery, radiation retinopathy, and bone marrow transplant retinopathy; proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; punctate inner choroidopathy, acute posterior multifocal placoid pigment epitheliopathy, myopic retinal degeneration, acute retinal pigement epitheliitis, retinitis pigmentosa, proliferative vitreal retinopathy (PVR), age-related macular degeneration (ARMD), diabetic retinopathy, diabetic macular edema, retinal detachment, retinal tear, uveitus, cytomegalovirus retinitis, glaucoma, amblyopia, stroke-induced blindness, visual dysfunction in Parkinson's disease, Alzheimer's disease and multiple sclerosis, seizure-induced cortical blindness, induced visual dysfunction, and epileptic blindness.

DESCRIPTION OF THE DRAWINGS

FIG. 1 shows the ability of selected amino acids to inhibit D-serine transport into neurons (rat brain synaptosomes) and glia (rat hippocampal astrocytes). Values are the concentration of amino acid required to inhibit 50% of [$^3$H]D-serine transport ($IC_{50}$) in μM, and are the means of at least two determinations. L-GPNA: L-γ-nitrophenyl glutamyl anilide.

FIG. 1A represents a graph displaying the electrophysiological recording from rat hippocampal slices and showing that L-4OHPG (L-4-hydroxyphenylglycine) potentiates NMDA receptor-mediated excitatory postsynaptic currents ($EPSC_{NMDA}$). The representative experiment shows that the potentiation effect of L-4OHPG (1000 μM) lasted for one hour and then returned to baseline in control buffer. 1000 is the concentration of L-4OHPG in μM and 22% refers to the percentage increase in the amplitude of $EPSC_{NMDA}$. Dots represent the amplitudes of $EPSC_{NMDA}$. Filled triangles represent control; open circles represent 1 μM 7-CKY and filled circles represent 1000 μM L-4OHPG. 7-CKY is a competitive inhibitor at the D-serine site of the NMDA receptor, which inhibits the NMDA receptor-mediated EPSCs and increases the sensitivity of $EPSC_{NMDA}$ to D-serine.

FIG. 1B represents a graph featuring summary data showing the dose-dependent effects of L-4OHPG on $EPSC_{NMDA}$.

FIG. 2A represents a graph showing that L-4OHPG dose-dependently facilitates long-term potentiation (LTP) in the primary visual cortex of rats.

FIG. 2B represents a graph that features the results of exposing visual cortex slices to D-amino acid oxidase (DAAO), an enzyme that selectively degrades extracellular D-serine. The data suggest that L-4OHPG's enhancement of LTP in the visual cortex slice of rats is dependent on extracellular D-serine.

FIG. 3A represents a graph that shows the correlation between the ability of compounds to inhibit neuronal D-serine transport and the threshold concentration required to enhance LTP in the visual cortex slice. The $r^2$ value (correlation coefficient) and p value (probability) indicates that no significant correlation exists.

FIG. 3B represents a graph that shows the correlation between the ability of compounds to inhibit astrocyte D-serine transport and the threshold concentration required to enhance LTP in the visual cortex slice. The $r^2$ value (correlation coefficient) and p value (probability) indicates that a highly significant correlation exists.

FIG. 4 represents a graph that shows the 2-component inhibition of D-serine transport into astrocytes by L-glutamine and L-trans-4-hydroxyproline (L-t-4OHPro) and $IC_{50}$ values for the individual components. Two-component inhibition curves were fitted using an algorithm available in GraphPad Prism 4. "Component 1" is the high affinity component and "Component 2" is the low affinity component. "Fraction" refers to the proportion that each component contributes to the total inhibition.

FIG. 5 represents a graph that shows the inhibition of transport into HEK cell lines expressing ASCT1 and ASCT2 by L-glutamine and L-t-4OHPro.

FIG. 6A represents a graph that shows transport of [$^3$H]D-serine into HEK cells expressing ASCT1 or ASCT2. Transport was measured in the presence (control) and in the absence (zero Na) of extracellular sodium.

FIG. 6B represents a graph that shows the inhibition of [³H]L-serine transport into astrocytes and HEK cells expressing ASCT1 and ASCT2 by D-serine.

FIG. 2 shows $IC_{50}$ values for the inhibition of [³H]L-serine transport into astrocytes and HEK cells expressing recombinant human ASCT1 or ASCT2. Values are $IC_{50}$'s in μM from 6-12 point inhibition curves, with an n of at least 2. For L-trans-4-hydroxyproline (L-t-4OHPro) and L-GPNA, two components of inhibition were present in the astrocyte assay, and *values are presented for the high and low affinity components. For comparison, threshold concentrations for the enhancement of LTP in rat visual cortex slices are shown.

FIG. 7 represents the correlation of the $IC_{50}$ values from the transport assays (see FIG. 2 and accompanying explanation) with the LTP threshold data (see FIG. 2A and accompanying explanation). Graph A shows the correlation between the $IC_{50}$ values for the ASCT1 transporter (also known as SLC1A4) and the LTP threshold data; graph B shows the correlation between the $IC_{50}$ values for the ASCT2 transporter (also known as SLC1A5) and the LTP threshold data; graph C shows the correlation between the product of both ASCT1's and ASCT2's $IC_{50}$ values and the LTP threshold data in order to take into account how contributions from both transporters might be important to produce the LTP enhancement (this plot gives the best correlation and suggests that inhibition of both transporters, leads to optimal LTP enhancement).

FIG. 8 shows that L-4OHPG enhances visual function in normal rats as assessed by sweep VEP. Saline was used as a control. Half of the rats were injected with 30 mg/kg L-4OHPG and the other half with saline in the first test; cross-over exposure took place one week later; the spatial frequencies were swept from 0.03 cycles per degree (cpd) to 1.6 cpd. Graphs A and B show visual acuity (VA) values for each rat measured before and 30 min after saline (A) or L-4OHPG (B) injection, and the average VA values from all rats are shown in D. The changes in VA measures are shown in C and E.

FIG. 9 shows that L-4-fluorophenylglycine (L-FPG) enhances visual function in normal rats as assessed by sweep VEP. Saline was used as a control. Half of the rats were injected with 10 mg/kg L-FPG and the other half with saline in the first test; cross-over exposure took place one week later; the spatial frequencies were swept from 0.03 cpd to 1.6 cpd. VA before and 40 min after L-FPG (graph A) or saline (graph B) injection are compared in individual rats and the average VA values are shown in D. The changes in VA measures are shown in C and E.

FIG. 10 shows the visual enhancement effect of L-4OHPG in the ONC rat. Saline was used as a control. Half of the rats were injected with 30 mg/kg L-4OHPG and the other half with saline in the first test; cross-over exposure took place one week later; the spatial frequencies were fixed at 0.2 cpd. Graph A and Graph B show data collected 30 min before and after L-4OHPG or saline injection. The changes in the power of signals are shown in C and D.

FIG. 11 shows that L-4OHPG enhances visual function in normal rabbits as assessed by sweep VEP. Saline was used as a control. Half of the rats were inject with 30 mg/kg L-4OHPG and the other half with saline in the first test; cross-over exposure took place one week later. the spatial frequencies were swept from 0.03 cycles per degree (cpd) to 1.6 cpd.

FIG. 12 shows that 4-FPG improved the contrast sensitivity impaired in rats fifty-three weeks after blue-light treatment. Saline was used as a control. Half of the rats were injected with 10 mg/kg 4-FPG and the other half with saline in the first test; cross-over exposure took place one week later; the spatial frequencies were fixed at 0.575 cpd.

DETAILED DESCRIPTION OF THE INVENTION

In one aspect the invention relates to a method for the treatment of visual system disorders caused by a deficit in N-methyl-D-aspartate receptor function, the method comprising administering to a subject in need thereof an ophthalmically acceptable pharmaceutical composition containing a therapeutically effective amount of one or more D-serine transporter inhibitor compounds.

In another aspect the invention relates to a method for the treatment of visual system disorders, the method comprising administering to a subject in need thereof an ophthalmically acceptable pharmaceutical composition containing a therapeutically effective amount of one or more D-serine transporter inhibitor compounds selected from the Glycine/Alanine family, the Glutamine/Asparagine family, the Tryptophan Family, the Phenylglycine family, the Phenylalanine family, the Cysteine family, the Serine/Threonine family, the Cyclic Amino Acid family and the Proline family.

In another aspect the invention relates to a method for the treatment of visual system disorders, the method comprising administering to a subject in need thereof an ophthalmically acceptable pharmaceutical composition containing a therapeutically effective amount of one or more D-serine transporter inhibitor compounds selected from L-gamma-glutamyl-4-nitroanilide, L-4-hydroxyphenylglycine, L-4-fluorophenylglycine, L-phenylglycine, trans-4-hydroxy-L-proline and R-gamma-2,4-dichlorobenzyl-L-proline.

In another aspect the invention relates to a pharmaceutical composition comprising as active ingredient a therapeutically effective amount of at least one D-serine transporter inhibitor compound and a pharmaceutically acceptable adjuvant, diluents or carrier.

In another aspect the invention relates to a method for the treatment of visual system disorders caused by a deficit in N-methyl-D-aspartate receptor function, the method comprising administering to a subject in need thereof an ophthalmically acceptable pharmaceutical composition containing a therapeutically effective amount of at least one or more ASCT1 inhibitor compounds and/or at least one or more ASCT1 inhibitor compounds.

In another aspect the invention relates to a pharmaceutical composition comprising as active ingredient a therapeutically effective amount of at least one or more ASCT1 inhibitor and/or at least one or more ASCT2 inhibitor and a pharmaceutically acceptable adjuvant, diluents or carrier.

In another aspect the invention relates to a method for the enhancement of visual function, the method comprising administering to a subject in need thereof an ophthalmically acceptable pharmaceutical composition containing a therapeutically effective amount of one or more D-serine transporter inhibitor compounds.

In another aspect the invention relates to a method for the enhancement of visual function, the method comprising administering to a subject in need thereof an ophthalmically acceptable pharmaceutical composition containing a therapeutically effective amount of one or more D-serine transporter inhibitor compounds selected from the group consisting of the Glycine/Alanine family, the Glutamine/Asparagine family, the Tryptophan Family, the Phenylglycine family, the Phenylalanine family, the Cysteine family, the Serine/Threonine family, the Cyclic Amino Acid family and the Proline family.

In another aspect the invention relates to a method for the enhancement of visual function, the method comprising administering to a subject in need thereof an ophthalmically acceptable pharmaceutical composition containing a therapeutically effective amount of one or more D-serine transporter inhibitor compounds selected from the group consisting of L-gamma-glutamyl-4-nitroanilide, L-4-hydroxyphenylglycine, L-4-fluorophenylglycine, L-phenylglycine, trans-4-hydroxy-L-proline and R-gamma-2,4-dichlorobenzyl-L-proline.

In another aspect the invention relates to a method for the enhancement of visual function, the method comprising administering to a subject in need thereof an ophthalmically acceptable pharmaceutical composition containing a therapeutically effective amount of at least one or more ASCT1 inhibitor and/or at least one or more ASCT2 inhibitor compounds.

In another aspect the invention relates to a pharmaceutical composition comprising as active ingredient a therapeutically effective amount of L-gamma-glutamyl-4-nitroanilide and a pharmaceutically acceptable adjuvant, diluents or carrier.

In another aspect the invention relates to a pharmaceutical composition comprising as active ingredient a therapeutically effective amount of L-4-hydroxyphenylglycine and a pharmaceutically acceptable adjuvant, diluents or carrier.

In another aspect the invention relates to a pharmaceutical composition comprising as active ingredient a therapeutically effective amount of L-4-fluorophenylglycine and a pharmaceutically acceptable adjuvant, diluents or carrier.

In another aspect the invention relates to a pharmaceutical composition comprising as active ingredient a therapeutically effective amount of L-phenylglycine and a pharmaceutically acceptable adjuvant, diluents or carrier.

In another aspect the invention relates to a pharmaceutical composition comprising as active ingredient a therapeutically effective amount of trans-4-hydroxy-L-proline and a pharmaceutically acceptable adjuvant, diluents or carrier.

In another aspect the invention relates to a pharmaceutical composition comprising as active ingredient a therapeutically effective amount of R-gamma-2,4-dichlorobenzyl-L-proline and a pharmaceutically acceptable adjuvant, diluents or carrier.

In another aspect, the present invention relates to pharmaceutical compositions comprising D-serine transporter inhibitors and therapeutic methods using such pharmaceutical compositions in methods for the treatment of visual system disorders.

In another aspect, the present invention relates to a method for the enhancement of visual function comprising administration of one or more D-serine transporter inhibitors by different administration routes. D-serine transporter inhibitors were identified as compounds that inhibit transport mechanisms in neurons and astrocytes, in D-serine transport assays in vitro.

Enhancement of visual function means administering one or more of the D-serine transport inhibitor compounds to improve the visual function, to alleviate its severity, to prevent the onset of a disorder, and to prevent its reoccurrence. Visual function includes visual acuity, visual field, night vision, color vision, dark/light adaptation, contrast sensitivity, binocular vision, motion detection, etc.

In another aspect the present invention relates to a pharmaceutical composition comprising a therapeutically effective amount of at least one D-serine transporter inhibitor compound, said compound being present alone or in combination with one or more pharmaceutically acceptable excipients.

In another aspect the present invention relates to a method for the treatment of visual system disorders caused by a deficit in N-methyl-D-aspartate receptor function, the method comprising administering to a subject in need thereof an ophthalmically acceptable pharmaceutical composition containing a therapeutically effective amount of one or more D-serine transporter inhibitor compounds.

In another aspect the present invention relates to a pharmaceutical composition comprising a therapeutically effective amount of at least one compound selected from the group consisting of ASCT1 inhibitor, ASCT2 inhibitor, and combinations thereof, said compound being present alone or in combination with one or more pharmaceutically acceptable excipients.

In another aspect the present invention relates to a method for the treatment of visual system disorders caused by a deficit in N-methyl-D-aspartate receptor function, the method comprising administering to a subject in need thereof an ophthalmically acceptable pharmaceutical composition containing a therapeutically effective amount of one or more compounds selected from the group consisting of ASCT1 inhibitor, ASCT2 inhibitor, and combinations thereof.

In another aspect the present invention relates to a method for the enhancement of visual function, the method comprising administering to a subject in need thereof an ophthalmically acceptable pharmaceutical composition containing a therapeutically effective amount of one or more compounds selected from the group consisting of ASCT1 inhibitor, ASCT2 inhibitor, and combinations thereof.

In another aspect the present invention relates to a method for the treatment of visual system disorders caused by a deficit in N-methyl-D-aspartate receptor function, the method comprising administering to a subject in need thereof an ophthalmically acceptable pharmaceutical composition containing a therapeutically effective amount of L-gamma-glutamyl-4-nitroanilide L-4-hydroxyphenylglycine, L-4-fluorophenylglycine, L-phenylglycine, trans-4-hydroxy-L-proline, R-gamma-2,4-dichlorobenzyl-L-proline.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back of the eye, front of the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

An opthalmically acceptable pharmaceutical composition is one that can be administered topically to the eye of a subject in need thereof. Comfort to the subject being administered the composition should be maximized, but other considerations, such as drug stability, may necessitate a pharmaceutical composition that provides less than optimal comfort. In such a case, the composition should be formulated such that it is tolerable to a subject being administered the composition topically.

The claimed pharmaceutical composition can be administered topically in the form of solutions or suspensions, ointments, gels, creams, etc. A "pharmaceutically acceptable excipient" is one that is compatible with the active ingredient of the composition and not harmful to the subject being administered the pharmaceutical composition. Solutions for ophthalmic application are often prepared using physiological saline as a major vehicle. Other vehicles include polyvinyl alcohol, povidone, hydroxypropyl methyl cellulose, poloxamers, carboxymethyl cellulose, hydroxyethyl cellulose, and purified water. Examples of useful excipients also include preservatives, buffers, other pH adjustors, tonicity adjustors, surfactants, antioxidants, and chelating agents.

Useful preservatives include benzalkonium chloride, chlorobutanol, thimerosal, phenylmercuric acetate and phenylmercuric nitrate. Examples of buffers include phosphate, borate, sulfate, acetate, and citrate buffers. Acids or bases may be used to adjust the pH of the compositions as needed. Examples of tonicity agents include glycerin, mannitol, sodium chloride and potassium chloride. Useful surfactants include, for example, Tween 80. Examples of ophthalmically acceptable antioxidants include sodium metabisulfite, sodium thiosulfate, acetylcysteine, butylated hydroxyanisole and butylated hydroxytoluene. A useful chelating agent is edentate disodium.

Mixtures of two or more of any suitable excipients may be used.

Aside from topical application to treat diseases affecting the eye including glaucoma, pharmaceutical compositions containing at least one compound of formula (I) can also be administered periocularly, intraocularly, or by other effective means available in the art.

Persons skilled in the art would readily understand that a drug containing one or more of the compounds disclosed herein can be confected as a powder, pill, tablet or the like, or as a solution, emulsion, suspension, aerosol, syrup or elixir suitable for oral or parenteral administration or inhalation. For solid dosage forms or medicaments, non-toxic solid excipients for admixture with compounds disclosed herein include, but are not limited to, pharmaceutical grades of mannitol, lactose, starch, magnesium stearate, sodium saccharin, polyalkylene glycols, talcum, cellulose, glucose, sucrose, and magnesium carbonate. The solid dosage forms may be coated by a material such as glyceryl monostearate or glyceryl distearate, which is utilized in known techniques to delay disintegration and absorption in the gastrointestinal tract for the purpose of providing a sustained action over a longer period. Solid dosage forms may also be coated by the techniques described in U.S. Pat. Nos. 4,256,108, 4,166,452 and 4,265,874 to form osmotic therapeutic tablets for control release.

Pharmaceutically administrable liquid dosage forms can, for example, comprise a solution or suspension of at least one of the compounds disclosed herein and optional pharmaceutical adjutants in a carrier, such as water, saline, aqueous dextrose, glycerol, ethanol and the like. The liquid dosage forms may also contain nontoxic auxiliary substances such as wetting or emulsifying agents, pH buffering agents and the like. Examples of such auxiliary agents include sodium acetate, sorbitan monolaurate, triethanolamine, sodium acetate, triethanolamine oleate, etc. Methods for preparing such dosage forms are well-known to persons skilled in the art (see, for example, Reminton's Pharmaceutical Sciences, Mack Publishing Company, Easton, Pa., 16$^{th}$ Edition, 1980).

Parenteral administration is generally characterized by subcutaneous, intramuscular, or intravenous injection. Injectables can be prepared as liquid solutions or suspensions, solid forms that can be reconstituted into solutions or suspensions prior to injection, or as emulsions. Suitable excipients include water, saline dextrose, glycerol, ethanol and the like. Such injectable pharmaceutical compositions may also contain minor amounts of non-toxic auxiliary substances such as wetting or emulsifying agents, pH buffers and the like.

Examples mentioned herein are not intended to limit the scope of the invention in any way.

Using D-serine transport assays in vitro, we have identified compounds that inhibit transport mechanisms in neurons and astrocytes. In Table 1, the activities of amino acid analogs to inhibit D-serine transport are shown. Under the assay conditions used, the sodium-independent transport of D-serine by rodent forebrain synaptosomes is mediated by asc-1 (Rutter et al., 2007), and the sodium-dependent transport of D-serine into astrocytes in culture is mediated by an ASCT transporter, ASCT2 according to the literature (Ribeiro et al., 2002).

The data from Table 1 shows that transport of D-serine into neurons and into astrocytes can be pharmacologically distinguished. Analogs of glutamine, phenylglycine, asparagine, cysteine and proline were able to select between the two transport systems.

To determine the effects of transport inhibition on NMDA receptor function, compounds were tested for their ability to affect NMDA receptor-mediated synaptic responses in brain slice preparations. L-4-hydroxyphenylglycine (L-4OHPG) potentiated NMDA receptor mediated excitatory post-synaptic currents (EPSC's) in the CA1 region of the hippocampus (FIG. 1A and FIG. 1B). In the visual cortex slice, LTP evoked by theta burst stimulation was enhanced by L-4OHPG. L-4OHPG enhanced LTP in a concentration-dependent manner, and its effects were completely prevented by inclusion of D-AAO in the perfusion medium, indicating that its ability to enhance synaptic plasticity was dependent on extracellular D-serine (FIG. 2B). Importantly, none of the compounds identified as D-serine transport inhibitors had significant direct effects on the NMDA receptor (or other glutamate receptor sub-types) as assessed in cultured hippocampal neurons.

In an attempt to understand the relative contributions of the neuronal and astrocyte D-serine transporters to the observed ability of compounds to enhance NMDA receptor-mediated responses, correlations were made between the effects of compounds in the transport assays and in the visual cortex slice LTP assay. A poor correlation was found between the effects in the neuronal transport assay and LTP (FIG. 3A, $r^2$=0.047) however an excellent correlation existed between the effects in the astrocyte transport assay and LTP (FIG. 3B, $r^2$=0.902). This indicated that the transporters present in astrocytes are those that regulate extracellular D-serine to influence NMDA receptor-mediated synaptic events.

The sodium-dependent D-serine transporter in astrocytes has been reported to be ASCT2 (Ribeiro et al., 2002). In the D-serine transport experiments in astrocytes, we noticed that some compounds produced inhibition curves that exhibited two components, suggesting that more than one transport component was present. In particular, two compounds defined the two components. L-glutamine showed higher affinity for a component that represented approximately 40% of the D-serine transport, and L-trans-4-hydroxyproline (L-t-4OHPro) showed higher affinity for a component that represented approximately 60% of the D-serine transport (FIG. 4). Competition studies with each of these compounds in the presence of the other indicated that L-glutamine had high affinity for the component with low affinity for L-t-4OHPro and vice versa. PCR studies have indicated that both ASCT1 and ASCT2 transporter sub-types are present in astrocytes (Yamamoto et al., 2004). However, functional expression of ASCT1 and ASCT2 in heterologous systems has indicated that, unlike ASCT2, ASCT1 does not transport D-serine (Shafqat et al., 1993). L-glutamine is reported to have high affinity for ASCT2 (range of 23-70 µM; Utsunomiya-Tate et al., 1996; Broer et al., 1999; Torres-Zamorano et al., 1998), and one report indicates that L-t-4OHPro has high affinity for ASCT1 (Pinilla-Tenas et al., 2003). We confirmed the selectivity of L-glutamine and L-t-4OHPro for the ASCT sub-types by examining transport in HEK cells heterologously expressing human ASCT1 and ASCT2. For these experiments, [$^3$H]L-serine was used since it is a high affinity substrate for both sub-types. As shown in FIG. 5, L-glutamine inhibited transport and showed selectivity towards ASCT2, whereas L-t-4OHPro showed selectivity towards ASCT1. Consequently, the two components of transport observed in astrocytes most likely represent ASCT1 (L-t-4OHPro-preferring) and ASCT2 (L-glutamine-preferring). If this is the case, however, it would suggest that ASCT1 does indeed transport D-serine, contrary to the literature report (Pinilla-Tenas et al., 2003). To investigate this, we examined transport into ASCT1-expressing HEK cells. As shown in FIG. 6A, [$^3$H]D-serine was transported into ASCT1-expressing HEK cells in a sodium-dependent manner and to a similar degree to the transport observed in ASCT2-expressing HEK cells. In addition, [$^3$H]L-serine transport was completely inhibited by D-serine in astrocytes and ASCT1 and ASCT2-expressing HEK cell lines (FIG. 6B) as would be expected if D-serine interacts with both transporter sub-types. Consequently, we have discovered that D-serine is indeed a substrate for ASCT1 with an affinity similar to that for ASCT2.

Given this evidence that transport into astrocytes is mediated by both ASCT1 and ASCT2, which of these transporter sub-types is primarily responsible for the inhibition of D-serine transport that leads to the enhancement of LTP observed? To address this, we examined the ability of the inhibitors identified in the astrocyte transport assay and that enhance LTP to inhibit transport in the HEK cells expressing each ASCT sub-type. As shown in Table 2, L-glutamine and the L-glutamine analog L-gamma-glutamyl-4-nitroanilide (L-GPNA) were selective for ASCT2. L-trans-4OHPro was selective for ASCT1. The phenylglycine analogs, isomers of serine, asparagine and cyclopropylglycine showed equal ability to inhibit both sub-types. Correlations between the IC$_{50}$ values for transport inhibition at the sub-types and the threshold concentrations to enhance LTP revealed no significant correlation with ASCT1 (FIG. 7a) but a significant correlation with ASCT2 (FIG. 7b), however the best correlation was obtained when the contribution of both sub-types was taken into account (product of the $IC_{50}$'s for both ASCT1 and ASCT2; FIG. 7c). This suggests that both sub-types are important for the enhancement of LTP and that dual sub-type inhibitors are the most effective compounds.

Examples of D-Serine Transporter Inhibitors

It has been found that certain amino acids of the Glycine/Alanine family, the Glutamine/Asparagine family, the Tryptophan Family, the Phenylglycine family, the Phenylalanine family, the Cysteine family, the Serine/Threonine family, the Cyclic Amino Acid family and the Proline family are examples of D-serine transporter inhibitors.

The following are non-limiting examples of D-serine transporter inhibitors which are useful in the practice of the present invention. The amino acids that were tested for D-serine transport inhibition properties were obtained from Sigma-Aldrich, Tocris Bioscience, Tyger Chemical Scientific, Bachem, ChemBridge Corporation, Matrix Scientific, PI Chemicals Inc., Toronto Research Chemicals and Maybridge Chemicals.

Table of Active Compounds by Amino Acid Family
Criterion for activity: ≥25% inhibition of [$^3$H]D-serine transport into rat hippocampal astrocytes at 1 mM

| Compound | Isomer |
|---|---|
| Glycine/Alanine Family | |
| glycine | |
| alanine | L |
| 2-aminobutyrate | L |
| 2-allylglycine | DL |
| valine | L |
| 3-(methylamino)alanine | L |
| 1-aminocyclopropane-1-carboxylic acid | |
| 1-aminocyclobutane-1-carboxylic acid | |
| 1-aminocyclopentane-1-carboxylic acid | |
| α-cyclopropylglycine | L |
| phenylglycine | L |
| tetrazol-5yl glycine | DL |
| 3-thienylglycine | L |
| aminocyclohexyl acetic acid | L |
| aminofuran-2-yl acetic acid | L |
| amino-(2,3-dihydro-benzo[1,4]dioxin-6-yl)-acetic acid | DL |
| aminonaphthalen-1-yl acetic acid | L |
| aminobicyclo[2.2.1]hept-5-en-2-yl acetic acid | DL |
| dihydrophenylglycine | D |
| 1-adamantyl(amino)acetic acid | |
| 2-aminoadamantine-2-carboxylic acid | |
| 3-benzoylalanine | DL |
| 3-(2-thienyl)-alanine | L |
| 3-cyclopentyl-alanine | L |
| 3(2-naphthyl)-alanine | L |
| 3-benzothienylalanine | L |
| azidohomoalanine | L |
| homopropargylglycine | L |
| valine | L |
| norvaline | L |
| alanine | D |
| Glutamine/Asparagine Family | |
| glutamine | L |
| glutamate-γ-hydroxamate | L |
| glutamate-γ-4-nitroanilide | L |
| glutamate-γ-anilide | DL |
| glutamate-γ-(α-naphthylamide) | L |
| glutamate-γ-(β-naphthylamide) | L |
| glutamate-γ-(β-naphthylamide) | L |
| glutamate-γ-methylester | L |
| glutamate-γ-ethylester | L |
| asparagine | L |
| asparagine | D |
| N-4-phenylasparagine | DL |
| kynurenine | L |
| kynurenine | D |
| 3-hydroxy kynurenine | DL |
| 2-amino-succinic acid 4-ethylester | DL |
| aspartate benzyl ester | L |
| 6-diazo-5-oxo-norleucine | L |
| Tryptophan Family | |
| tryptophan | L |
| 6-fluorotryptophan | DL |
| 5-fluorotryptophan | L |
| 4-fluorotryptophan | DL |
| 5-hydroxytryptophan | L |
| Phenylglycine Family | |
| phenylglycine | L |
| 4-hydroxyphenylglycine | L |
| 4-fluorophenylglycine | L |
| 4-methoxyphenylglycine | DL |
| amino-(4-nitro-phenyl)-acetic acid | DL |
| 4-trifluoromethylphenylglycine | L |
| 3-hydroxyphenylglycine | L |
| amino-(3-fluoro-phenyl)-acetic acid | DL |
| amino-(3-bromo-phenyl)-acetic acid | DL |
| 3-trifluoromethylphenylglycine | DL |
| amino-(3-nitro-phenyl)-acetic acid | DL |
| 2-fluorophenylglycine | DL |
| amino-o-tolyl-acetic acid | L |
| 2-chlorophenylglycine | DL |
| 3,4-difluorophenylglycine | DL |
| 3-chloro-4-fluorophenylglycine | DL |
| 3-fluoro-4-methylphenylglycine | DL |
| 4-fluoro-3-methylphenylglycine | DL |
| 3-carboxy-4-hydroxyphenylglycine | L |
| 2-Cl, 5-OH phenylglycine | DL |
| 3,4-dihydroxyphenylglycine | DL |
| 3,5-dihydroxyphenylglycine | DL |
| 4-carboxy-3-hydroxyphenylglycine | DL |
| 2-phenylglycine methylester | L |
| (4-methoxyphenyl)(methylamino)acetic acid | DL |
| 2-hydroxyphenylglycine | DL |
| amino-(2,3-dihydrobenzo [1,4]dioxin-6-yl) acetic acid | DL |
| amino-benzo[1,3]dioxo1-5-yl acetic acid | DL |
| 2-amino-2-[3-hydroxy-4-(hydroxymethyl)phenyl]acetic acid | DL |
| (4-fluorophenyl)-morpholin-4yl-acetic acid | DL |
| cyclopropylalanine | L |
| Phenylalanine Family | |
| homophenylalanine | L |
| 2-amino-5-phenylpentanoic acid | L |
| 4-hydroxyphenylalanine | L |
| 3,4-dihydroxyphenylalanine | L |
| Quisqualic acid | L |
| Cysteine Family | |
| cysteine | L |
| S-methyl-cysteine | L |
| S-ethyl-cysteine | L |
| S-phenyl-cysteine | L |
| S-benzyl-cysteine | L |
| S-(4-methylphenyl)-cysteine | L |
| penicillamine | L |
| homocysteine | L |
| Serine/Threonine Family | |
| serine | L |
| serine | D |
| threonine | L |
| threonine | D |
| threonine | L-allo |
| threonine | DL-allo |
| O-methylserine | DL |

Table of Active Compounds by Amino Acid Family
Criterion for activity: ≥25% inhibition of [³H]D-serine transport into rat hippocampal astrocytes at 1 mM

| Compound | Isomer |
|---|---|
| O-acetylserine | L |
| benzylserine | L |
| beta (2-thienyl)serine | DL |
| 3-pyridylserine | DL |
| serine methylester | L |
| serine-beta-naphthylamide | L |
| methionine | L |
| 4-hydroxy-isoleucine | L |
| homoserine | D |
| homoserine | L |
| Cyclic Amino Acid Family | |
| 1-amino-1-carboxycyclopropane | |
| 1-amino-1-carboxycyclobutane | |
| 1-amino-1-carboxycyclopentane | |
| homocysteine thiolactone | L |
| homoserine lactone | L |
| Proline Family | |
| proline | L |
| 3,4-dehydroproline | L |
| 4-hydroxy-L-proline | trans |
| 4-fluoro-L-proline | trans |
| 4-fluoro-L-proline | cis |
| γ-benzyl-L-proline | R |
| γ-(4-fluorobenzyl)-L-proline | R |
| 1,2,3,4-tetrahydro-3-isoquinolinecarboxylic acid | S |
| 2,3,4,9-tetrahydro-1H-beta-carboline-3-carboxylic acid | DL |
| 2,3-dihydro-1H-isoindole-1-carboxylic acid | DL |
| 4H-thieno[3,2-b]pyrrole-5-carboxylic acid | |
| azetidine-2-carboxylic acid | L |
| proline-beta naphthylamide | L |
| trans-4-cyclohexylproline | L |
| trans-4-hydroxyproline-naphthylamide | L |
| 4,6-Dichloro-3-[(1E)-3-oxo-3-(phenylamino)-1-propenyl]-1H-indole-2-carboxylic acid | |
| (2S,3S,4S)-Carboxy-4-(1-methylethenyl)-3-pyrrolidineacetic acid 4-methoxy-7-nitro-1H-indolinyl amide | |
| (E)-4,6-Dichloro-3-(2-phenyl-2-carboxyethenyl)indole-2-carboxylic acid | |
| γ-allyl-L-proline | R |
| aziridine-2-carboxylic acid | L |
| γ-(4-nitrobenzyl)-L-proline | R |
| trans-4-phenylproline | L |
| γ-(3,4-difluorobenzyl)-L-proline | R |
| γ-(3-thienylmethyl)-L-proline | R |
| γ-(4-methylbenzyl)-L-proline | R |
| γ-(2-naphthylenylmethyl)-L-proline | R |
| γ-propynyl-L-proline | R |
| γ-(3-fluorobenzyl)-L-proline | R |
| γ-(2-fluorobenzyl)-L-proline | R |
| γ-(4-bromobenzyl)-L-proline | R |
| γ-(4-chlorobenzyl)-L-proline HCl | R |
| γ-(4-iodobenzyl)-L-proline HCl | R |
| 4H-thieno[3,2-b]pyrrole-5-carboxylic acid | |
| γ-(2-trifluromethylbenzyl)-L-proline HCl | R |
| γ-(4-tertbutylbenzyl)-L-proline HCl | R |
| 3-phenylproline | |
| γ-(2-cyanobenzyl)-L-proline HCl | R |
| γ-(2-methylbenzyl)-L-proline HCl | R |
| γ-(3-trifluoromethyl-benzyl)-L-proline HCl | R |
| γ-(3-phenyl-allyl)-L-proline HCl (Boc?) | R |
| γ-(1-naphthalenylmethyl)-L-proline HCl | R |
| 4-(3-chlorobenzyl)pyrrolidine-2-carboxylic acid HCl | 2S, 4S |
| 4-(3-chlorobenzyl)pyrrolidine-2-carboxylic acid HCl | 2S, 4R |
| 4-benzyl-L-proline | S |
| γ-(2-furanylmethyl)-L-proline | S |
| γ-(3-chlorobenzyl)-L-proline HCl | R |
| γ-(2-pyridinylmethyl)-L-proline 2HCl | S |
| 4-(3-chlorophenoxy)pyrrolidine-2-carboxylic acid HCl | 2S, 4R |
| 4-(3-chlorophenoxy)pyrrolidine-2-carboxylic acid HCl | 2S, 4S |
| γ-(2-iodobenzyl)-L-proline HCl | R |
| γ-(3-benzothienylmethyl)-L-proline HCl | R |
| γ-(2-bromobenzyl)-L-proline HCl | R |
| γ-(4-trifuoromethylbenzyl)-L-proline HCl | R |
| γ-(3-bromobenzyl)-L-proline HCl | R |
| γ-(4-pyridinylmethyl)-L-proline HCl | R |
| γ-(4-cyanobenzyl)-L-proline HCl | R |
| γ-(3-cyanobenzyl)-L-proline HCl | R |
| γ-(3,4-dichlorobenzyl)-L-proline HCl | R |
| γ-(2-chlorobenzyl)-L-proline HCl | R |
| γ-(2,4-dichlorobenzyl)-L-proline HCl | R |
| γ-propynyl-L-proline HCl | R |
| γ-(2-cyanobenzyl)-L-proline HCl | R |
| 3-methyl-2-pyrrolidine-2-carboxylic acid | 2S, 3S |
| 3-phenyl-2-pyrrolidine-2-carboxylic acid | 2S, 3R |
| (E)-4,6-Dichloro-3-(2-phenyl-2-carboxyethenyl)indole-2-carboxylic acid | |
| 4,6-Dichloro-3-[(1E)-3-oxo-3-(phenylamino)-1-propenyl]-1H-indole-2-carboxylic acid | |
| Carboxy-4-(1-methylethenyl)-3-pyrrolidineacetic acid 4-methoxy-7-nitro-1H-indolinyl amide | (2S, 3S, 4S) |

The compounds identified here in assays of D-serine transport are inhibitors of the transporter sub-types ASCT1 (SLC1A4) and ASCT2 (SLC1A5), as confirmed is transport assays using HEK cells that heterologously express human ASCT1 or ASCT2. This includes the compounds L-gamma-glutamyl-4-nitroanilide, L-4-hydroxyphenylglycine, L-4-fluorophenylglycine, L-phenylglycine, trans-4-hydroxy-L-proline and R-gamma-2,4-dichlorobenzyl-L-proline. These compounds have $IC_{50}$ values less than 2 mM in one or both assays of transport in HEK cells expressing ASCT1 or ASCT2.

To investigate the ability of compounds to improve visual function in vivo, compounds identified in the transport and in vitro LTP assays were selected for study in rodent models. These experiments show that L-4OHPG and L-4FPG enhance visual function in normal rats as assessed by sweep VEP (FIGS. 8 and 9), and that L-4OHPG enhances visually-evoked signals from the visual cortex in rats with optic nerve crush (FIG. 10). L-4OHPG also enhanced sweep VEP in normal rabbits (FIG. 11). In a model of macular degeneration, rats with damaged retinas following blue-light treatment were found to have a deficit in contrast sensitivity. Treatment with L-4OHPG showed a significant improvement in contrast sensitivity, restoring it towards normal levels (FIG. 12). Thus, we have shown that compounds which inhibit D-serine transport can improve visual performance in normal rats and rabbits and in a two retinal disease models where visual performance has been impaired.

General Procedures Followed in Obtaining Experimental Data

Electrophysiological Recording from Rat Hippocampal Slices (FIGS. 1A-1B):

350 μM thick hippocampal slices were prepared from 21- to 35-year-old rats using Leica VT1000S-microtome. Slices were perfused with ACSF containing: 121 mM NaCl, 2.5 mM KCl, 2.0 mM $Mg_2SO_4$, 2.0 $CaCl_2$, 1 mM $NaH_2PO_4$, 26.2 $NaHCO_3$, and 11 mM glucose, which was equilibrated with 5% $CO_2$/95% $O_2$. Experiments were performed in a recording chamber on the stage of an Olympus BX-61wi microscope with infrared DIC optics for visualizing whole-cell patchclamp recordings. EPSPs were recorded from CA1 pyramidal neurons by stimulating the Schaffer collateral-commissural pathway using a bipolar tungsten electrode. The recording pipettes were filled with regular ICM containing: 120 mM Cs-gluconate, 5 mM NaCl, 10 mM KCl, 0.1 mM $CaCl_2$, 1 mM EGTA, 2 mM $MgCl_2$, 10 mM HEPES, 2 mM Na-ATP, 2 mM $Na_2$-phosphocreatine, and 0.25 mM Na-GTP, pH 7.3 (290 mOsm).

To measure NMDA-mediated EPSCs, extracellular $Mg_2SO_4$ was lowered to 0.2 mM and 2 μM NBQX and 100 μM picrotoxin were added in the ACSF. 1 μM 7-CKY (7-chlorokynurenic acid) was added to improve the sensitivity of $EPSC_{NMDA}$ to D-serine.

Long Term Potentiation in Primary Visual Cortex (FIG. 2)

Long Term Potentiation (LTP) in primary visual cortex has been used as a cellular model for visual cortex plasticity and has functional consequences on visual evoked responses. NMDA receptors play a critical role in visual cortex LTP induction.

Visual Cortex Slice Physiology:

Following decapitation of the rat, the brain was rapidly removed and immersed in ice-cold artificial cerebrospinal fluid (ACSF) containing 124 mM NaCl, 3 mM KCl, 1.25 mM $KH_2PO_4$, 3.4 mM $CaCl_2$, 2.5 mM $MgSO_4$, 26 mM $NaHCO_3$, and 10 mM D-glucose. A block of visual cortex was created by removing the frontal ⅔ portion of the brain and the cerebellum. Coronal visual cortex slices of 375 μm were prepared from adult Sprague Dawley (SD) rats using a vibratome (VT 1000 S; Leica). The slices were maintained in an interface recording chamber perfused with preheated ACSF. Slices were continuously perfused with this solution at a rate of 1.00-1.50 ml/min while the surface of the slices was exposed to warm, humidified 95% $O_2$/5% $CO_2$ and maintained at 31±1° C. Visual cortex slices were allowed to recover for 1 hr before recording began. A single stimulating and recording electrode were placed in layer IV and III, respectively, to generate and record a field excitatory postsynaptic potentials (fEPSPs). Pulses were administered every 20 s using a current that produced a fEPSP that was 50% of the maximum spike free response. An input-output (IO) curve was done to determine the stimulation needed to achieve a stable baseline. Following a 15 min stable baseline recording period, a train of 5 theta bursts (each burst containing four pulses at 100 Hz with an inter-burst interval of 200 ms) were delivered to the slice. This was repeated 2 additional times with a 1 minute intertrain interval, and the level of LTP was recorded for at least 30 min. Changes in amplitude of the synaptic response were used to measure the extent of LTP because it was determined to be the more consistent parameter than the slope of the response. Control LTP values were obtained from slices not treated with drug. Different slices were used to study drug effects on LTP. After a 15 min baseline recording period, the compounds of interest were infused for 15 minutes followed by LTP induction. Washout of the compounds began 5 minutes after tetanization. Recording of the amplitude before, during, and after drug infusion was done.

*DAAO Assay (FIG. 2B):

For experiments with DAAO, 0.2 unit/ml of DAAO were infused with or without the compounds of interest for 15 minutes before LTP induction.

*Sweep VEP (FIGS. 8-12):

Data gathered through the sweep visually evoked potential assessment (sweep VEP, sVEP) show that L-4FPG and L-4OHPG enhance visual function in normal rats and rabbit and that L-4OHPG enhances remaining visual function in rats with optic nerve crush.

Sweep visually evoked potential (sweep VEP, sVEP), which was first introduced by Regan [1] in 1973, has become an important technique to measure visual function. It is an objective method that can be used to assess visual acuity (VA) and contrast sensitivity (CS) in infants, young children and people with special needs. It was adapted to measure VA and CS in animals.

VEP Recording in Rats:

The recording electrodes were permanently implanted into the right visual cortex of Long Evans rats at lambda and 4.5 mm lateral to the midline, to a depth of 800 microns (layer III/iV). A reference electrode was placed epidurally on the midline 1.2 mm anterior to bregma. All recordings were conducted in awake rats starting at least two weeks after recovery from surgery. During recording the rats were alert and restrained in a home-made restrainer. They were habituated 2-3 times pre-surgery and at least three more times during seven days post-surgery. PowerDiva software from Anthony Norcia (Smith Kettlewell Institute of Visual Sciences) was used for data acquisition and analysis. Similar recording was performed in rabbits (FIG. 11) except the screw electrodes were place on top of the skull.

Visual Stimuli for Visual Acuity Measurement:

Stimuli were presented on a CRT computer monitor and consist of full-field sine-wave gratings at 80% contrast, reversing at 6.25 Hz. VEPs were elicited by horizontally oriented gratings. The display was positioned 24 cm in front of the rat and centered at the vertical meridian. Mean luminance was held constant at 20 cd. For sVEP in normal rats (slides 76-79), one stimulus presentation (one trial) consists of a spatial frequency sweep decreasing from 1.6 to 0.03 cycles/degree in 15 linear steps. A total of 20 trials were collected. Visual acuity (VA) thresholds were estimated using PowerDiva software. For fixed frequency stimulus in optic nerve crushed (ONC) rats (slides 80-83), the spatial frequency was fixed at 0.2 or 0.5 cycles/degree. Each trial lasts for 15 s. A total of 5 trials were collected and the signal powers were calculated.

Visual Stimuli for Contrast Sensitivity Measurement:

One stimulus presentation (one trial) consists of a contrast sweep increasing from 2.5 to 70% in 15 log steps. A total of 20 to 30 trials were collected. Contrast thresholds (CT) were estimated using PowerDiva software. Contrast sensitivity (CS) is calculated as 1/CT.

Blue-light treatment damages photoreceptors in the retina, and has been proposed as a model of age related macular degeneration (ARMD; Wielgus et al., 2010). In blue-light treated Long-Evans rats, contrast sensitivity, an important measure of visual performance, was significantly impaired. Transport experiments (FIGS. 1 and 2; FIGS. 4-6)

Cell-based assays: the transport of [$^3$H]L- or D-serine was measured in primary cultures of rat hippocampal astrocytes or in human embryonic kidney (HEK) cells expressing ASCT transporter sub-types. For the astrocyte assays, cells were plated on either 24- or 96-well plates at a density of 50,000 cells per well. For the HEK assays, cells were plated on coated 96-well plates at a density of 80,000 cells/well. Assays were conducted in duplicate at room temperature in assay buffer consisting of: NaCl: 150 mM, KCl: 2 mM; $MgCl_2$: 1 mM; $CaCl_2$: 1 mM; HEPES: Tris buffer: 10 mM, pH7.4. To assess the sodium-dependence of transport, NaCl was replaced in the assay buffer by equimolar choline chloride. Following aspiration of growth medium and 2 washes with assay buffer, cells were incubated with [$^3$H]L- or D-serine at a final concentration of 1 μM for 5 min (astrocytes) or 1 min (HEK cells), after which the incubation medium was aspirated and the cells washed twice with ice-cold assay buffer.

Cells containing radiolabel were solubilized in 100 μl of 1% Triton-X100 and an aliquot counted in a beta counter. $IC_{50}$ values were determined over a range of at least 6 concentrations and derived from curve-fitting algorithms available in Graph Pad Prism 4.

Synaptosome assays: a P2 fraction of rat forebrain was prepared and assayed immediately. Aliquots of the P2 preparation (approx. 1 mg of original tissue weight) were incubated in sodium-free assay buffer (CholineCl: 128 mM; KCl: 3.5 mM; $KH_2PO_4$: 1.5 mM; $MgCl_2$: 1 mM; $CaCl_2$: 1 mM; glucose: 10 mM; Tris-acetate buffer: 10 mM, pH7.4) containing [$^3$H]D-serine (final concentration of 50 nM) and test compounds in duplicate for 4 mins at room temperature. The synaptosomes containing radiolabel were collected by filtration onto Whatman GF/C filters, and washed twice with ice cold assay buffer. Filters were solubilized in scintillation fluid and radioactivity determined in a beta counter. $IC_{50}$ values were determined as described for the cell-based assays above.

What is claimed is:

1. A method for the treatment of visual system disorders caused by a deficit in N-methyl-D-aspartate receptor function, the method comprising administering to a subject in need thereof an ophthalmically acceptable pharmaceutical composition containing a therapeutically effective amount of one or more D-serine transporter inhibitor compounds.

2. The method for the treatment of visual system disorders, according to claim 1, the method comprising administering to a subject in need thereof an ophthalmically acceptable pharmaceutical composition containing a therapeutically effective amount of one or more D-serine transporter inhibitor compounds selected from the Glycine/Alanine family, the Glutamine/Asparagine family, the Tryptophan Family, the Phenylglycine family, the Phenylalanine family, the Cysteine family, the Serine/Threonine family, the Cyclic Amino Acid family and the Proline family.

3. The method for the treatment of visual system disorders, according to claim 2, the method comprising administering to a subject in need thereof an ophthalmically acceptable pharmaceutical composition containing a therapeutically effective amount of one or more D-serine transporter inhibitor compounds selected from L-gamma-glutamyl-4-nitroanilide, L-4-hydroxyphenylglycine, L-4-fluorophenylglycine, L-phenylglycine, trans-4-hydroxy-L-proline and R-gamma-2,4-dichlorobenzyl-L-proline.

4. The method for the treatment of visual system disorders, according to claim 3, the method comprising administering to a subject in need thereof an ophthalmically acceptable pharmaceutical composition containing a therapeutically effective amount of L-gamma-glutamyl-4-nitroanilide.

5. The method for the treatment of visual system disorders, according to claim 3, the method comprising administering to a subject in need thereof an ophthalmically acceptable pharmaceutical composition containing a therapeutically effective amount of L-4-hydroxyphenylglycine.

6. The method for the treatment of visual system disorders, according to claim 3, the method comprising administering to a subject in need thereof an ophthalmically acceptable pharmaceutical composition containing a therapeutically effective amount of L-4-fluorophenylglycine.

7. The method for the treatment of visual system disorders, according to claim 3, the method comprising administering to a subject in need thereof an ophthalmically acceptable pharmaceutical composition containing a therapeutically effective amount of L-phenylglycine.

8. The method for the treatment of visual system disorders, according to claim 3, the method comprising administering to a subject in need thereof an ophthalmically acceptable pharmaceutical composition containing a therapeutically effective amount of trans-4-hydroxy-L-proline.

9. The method for the treatment of visual system disorders, according to claim 3, the method comprising administering to a subject in need thereof an ophthalmically acceptable pharmaceutical composition containing a therapeutically effective amount of R-gamma-2,4-dichlorobenzyl-L-proline.

10. A pharmaceutical composition comprising as active ingredient a therapeutically effective amount of at least one D-serine transporter inhibitor compound and a pharmaceutically acceptable adjuvant, diluents or carrier.

11. A method for the enhancement of visual function, the method comprising administering to a subject in need thereof an ophthalmically acceptable pharmaceutical composition containing a therapeutically effective amount of one or more D-serine transporter inhibitor compounds.

12. The method for the enhancement of visual function, according to claim 11, the method comprising administering to a subject in need thereof an ophthalmically acceptable pharmaceutical composition containing a therapeutically effective amount of one or more D-serine transporter inhibitor compounds selected from the group consisting of the Glycine/Alanine family, the Glutamine/Asparagine family, the Tryptophan Family, the Phenylglycine family, the Phenylalanine family, the Cysteine family, the Serine/Threonine family, the Cyclic Amino Acid family and the Proline family.

13. The method for the enhancement of visual function, according to claim 12, the method comprising administering to a subject in need thereof an ophthalmically acceptable pharmaceutical composition containing a therapeutically effective amount of one or more D-serine transporter inhibitor compounds selected from the group consisting of L-gamma-glutamyl-4-nitroanilide, L-4-hydroxyphenylglycine, L-4-fluorophenylglycine, L-phenylglycine, and trans-4-hydroxy-L-proline.

14. The method for the enhancement of visual function, according to claim 13, the method comprising administering to a subject in need thereof an ophthalmically acceptable pharmaceutical composition containing a therapeutically effective amount of L-4-hydroxyphenylglycine.

15. The method for the enhancement of visual function, according to claim 13, the method comprising administering to a subject in need thereof an ophthalmically acceptable pharmaceutical composition containing a therapeutically effective amount of L-4-fluorophenylglycine.

16. The method for the enhancement of visual function, according to claim 13, the method comprising administering to a subject in need thereof an ophthalmically acceptable pharmaceutical composition containing a therapeutically effective amount of L-phenylglycine.

17. The method for the enhancement of visual function, according to claim 13, the method comprising administering to a subject in need thereof an ophthalmically acceptable pharmaceutical composition containing a therapeutically effective amount of L-gamma-glutamyl-4-nitroanilide.

18. The method for the enhancement of visual function, according to claim 13, the method comprising administering to a subject in need thereof an ophthalmically acceptable pharmaceutical composition containing a therapeutically effective amount of trans-4-hydroxy-L-proline.

19. The method for the enhancement of visual function, according to claim 13, the method comprising administering to a subject in need thereof an ophthalmically acceptable pharmaceutical composition containing a therapeutically effective amount of R-gamma-2,4-dichlorobenzyl-L-proline.

20. The pharmaceutical composition according to claim 10, wherein the D-serine inhibitor compound is selected from: L-gamma-glutamyl-4-nitroanilide, L-4-hydroxyphenylglycine, L-4-fluorophenylglycine, L-phenylglycine, trans-4-hydroxy-L-proline, or R-gamma-2,4-dichlorobenzyl-L-proline.

* * * * *